US008002698B2

(12) United States Patent
Motai et al.

(10) Patent No.: US 8,002,698 B2
(45) Date of Patent: Aug. 23, 2011

(54) THERAPEUTIC METHOD THAT USES OVERTUBE

(75) Inventors: Kousuke Motai, Tokyo (JP); Yoshio Onuki, Tokyo (JP); Yasuhito Kura, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 664 days.

(21) Appl. No.: 11/732,804

(22) Filed: Apr. 4, 2007

(65) Prior Publication Data
US 2008/0249356 A1    Oct. 9, 2008

(51) Int. Cl.
*A61B 1/00* (2006.01)
*A61B 19/00* (2006.01)

(52) U.S. Cl. ........ 600/115; 600/114; 600/116; 600/121; 128/898

(58) Field of Classification Search .................. 600/104, 600/106, 114–116, 120, 121; 604/500, 508–510, 604/528; 128/898; 606/45, 167, 191
See application file for complete search history.

(56) References Cited

U.S. PATENT DOCUMENTS
2006/0235269 A1 * 10/2006 Waxman ........................ 600/104

FOREIGN PATENT DOCUMENTS
JP    61-284225    12/1986

OTHER PUBLICATIONS

Kuno et al., Double-balloon enteroscopy through a Roux-en-Y anastomosis for EMR of an early carcinoma in the afferernt duodenal limb, Dec. 2004, Gastrointestinal Endoscopy, vol. 60, Issue 6, 1032-1034.*
Hirai et al., "An Oblique-Viewing Endoscope with an Overtube Fasilitate Bile Duct Stone Removal in Roux-en-Y Gastrectomy Patients", Gastroenterological Endoscopy (2006), vol. 48(2), pp. 212-217.
Satoh et al., "3 Cases of Endoscopic Treatments of Roux-en-Y Reconstructive Stomach Through Papilla-Effectiveness of Oblique-Viewing Endoscope and Small Intestine Overtube", Therapeutic Research for Hepato-Biliary-Pancreatic Diseases (2006), vol. 4, No. 1, p. 88.

* cited by examiner

*Primary Examiner* — Thomas J Sweet
*Assistant Examiner* — Ryan Henderson
(74) *Attorney, Agent, or Firm* — Scully, Scott, Murphy & Presser, P.C.

(57) ABSTRACT

With a first endoscope inserted through an overtube, the overtube is orally inserted into an object being examined, and a distal end portion of an insertion tube of the first endoscope is made to advance, within the object, from a jejunum via a jejunum-to-jejunum anastomosed portion and a jejunum-anastomosed bent portion so that the distal end portion is located adjacently to a Vater's papilla of a duodenum. The overtube is then sent to a position which is adjacent to the Vater's papilla along the insertion tube of the first endoscope. After this, the first endoscope is pulled from the overtube. A second endoscope is then inserted into the overtube to make a distal end portion of its insertion tube protrude from the distal end of the overtube and is located adjacently to the Vater's papilla. The second endoscope thus-approached is used to treat the Vater's papilla and the tissue therearound.

8 Claims, 26 Drawing Sheets

THERAPEUTIC METHOD THAT USES OVERTUBE

BACKGROUND OF THE INVENTION

1. Technical Field of the Invention

The present invention relates to a therapeutic method and an endoscopic system which use an overtube, and in particular, to the therapeutic method and the endoscopic system which use an overture and which are preferable to treatment on endoscopic retrograde cholangiopancreatography (ERCP) with patients who had a Roux-en-Y reconstructive operation.

2. Related Art

Endoscopic examinations and treatments for biliary disease and pancreas disease, such as biliary tract cancer, pancreas cancer, cholelithiasis, and common bile duct stone, are progressing at a rapid pace. Compared to the conventional surgical treatments, these examinations and treatments are less invasive and less burden on patients. The techniques for these examinations and treatments include endoscopic retrograde cholangiopancreatography (ERCP) and Endoscopic sphincterotomy. These endoscopic examinations and treatments are on the progress to applications to postgastrectomy cases.

The difficulty level of procedures largely depends on reconstruction performed after partial removal of the stomach or reconstruction performed after the total gastric resection. As to the procedural difficulty level after the stomach reception, a Billroth I reconstruction can be performed using the normal ERCP procedure. Meanwhile, in a Billroth II reconstruction and in the reconstruction performed after the total gastric resection, it has been considered that the procedure related to the ERCP is higher in the difficulty level.

The Roux-en-Y reconstructive operation is most frequently used as the reconstructive operation for the total gastric resection. In the following references, reported is a successful example of ERCP which uses an endoscope-dedicated overtube for the small intestine in the treatment of the common biliary duct stone on the Roux-en-Y reconstructive operation.

[Reference 1] Hirai et al., "An Oblique-viewing Endoscope with an Overtube Facilitate Bile Duct Stone Removal in Roux-en-Y Gastrectomy Patients," Gastroenterological Endoscopy 2006; 48: 212-217.

[Reference 2] Satoh et al., "3 cases of endoscopic treatments of Roux-en-Y reconstructive stomach through papilla—Effectiveness of Oblique-viewing Endoscope and Small Intestine Overtube," Therapeutic Research for Hepato-Biliary-Pancreatic Diseases, Vol. 4 No. 1, page 88, 2006.

These references show that the ERCP was performed with an oblique-viewing endoscope, in which the digestive tract was shortened by stretching operations of the endoscope, a small-intestine overtube was made to advance to suppress deformations of the digestive tract, and then the endoscope was made to advance. It is reported that, though being in all of a few cases, repeating these operations allowed to the endoscope to reach the duodenum papilla.

For using procedures with an oblique-viewing endoscope or a forward-viewing endoscope, it is easier to insert the endoscope into an object because the view in the inserting direction can be secured. However, in this case, it is difficult to perform treatment, because the view in the treating direction cannot be secured. Thus, it is easy for the endoscope to pass the overtube through the jejunum-anastomosed bent portion and to reach the papilla, while it is difficult to treat the papilla by the endoscope. If giving greater importance to easiness of the treatment of the papilla to the contrary, a side-viewing endoscope may be used. However, for the side-viewing endoscope, the view in the inserting direction cannot be secured, resulting in a lessened performance for inserting the endoscope. As stated, it is considerably difficult to make both the treatment and the inserting performance easier at the same time.

SUMMARY OF THE INVENTION

The present invention has been made in consideration of the problem that the foregoing overtubes for endoscopes has confronted, and has an object to provide a therapeutic method and an endoscopic system which use an overtube, the method and system of which are able to enable an endoscope to access the Vater's papilla of an Roux-en-Y gastrectomy patient in a speedy, stable and easy manner after smoothly passing the jejunum-to-jejunum anastomosed portion and jejunum-anastomosed bent portion.

According to the present invention, as one aspect thereof, there is provided an endoscopic system comprising: an overtube having an insertion channel formed along an axial direction thereof; an endoscope inserted into the insertion channel of the overtube for use thereof; and assist means for assisting, when the overtube is inserted adjacently to a jejunum-to-jejunum anastomosed portion of a jejunum of an object being examined in a state where the endoscope is kept being inserted into the insertion channel of the overtube, changes of an insertion path along which the overtube is inserted from the jejunum to the jejunum-to-jejunum anastomosed portion.

Furthermore, as another aspect of the present invention, there is provided a method of either diagnosing or treating a Vater's papilla and tissue located adjacently thereto, comprising: a first step in which a first endoscope is inserted into an insertion channel of an overtube; a second step in which, with the first endoscope inserted through the insertion channel of the overtube, the overtube is orally inserted into an object being examined and a distal end portion of an insertion tube of the first endoscope is located adjacently to a Vater's papilla of a duodenum of the object by making the distal end portion advance, in the object, from a jejunum via a jejunum-to-jejunum anastomosed portion and a jejunum-anastomosed bent portion; a third step in which the overtube is sent to a position adjacently to the Vater's papilla along an insertion tube of the first endoscope; a fourth step in which the first endoscope is pulled out of the insertion channel of the overtube; and a fifth step in which a second endoscope is inserted into the insertion channel of the overtube so as to enable a distal end portion of an insertion tube of the second endoscope to be protruded from a distal end of the overtube and to position the distal end portion adjacently to the Vater's papilla, the second endoscope being for diagnosis or treatment of the Vater's papilla and the tissue located adjacently thereto.

DETAILED DESCRIPTION OF PREFERRED EMBODIMENTS

Hereinafter, referring to the accompanying drawings, various embodiments and their modifications of an endoscopic system with an overtube according to the present invention will now be described.

In the embodiments, an endoscopic system and a therapeutic procedure which use the overtube according to the present invention is applied to a pancreatic/biliary duct treatment (a treatment of pancreatic and biliary ducts) to the Vater's papilla of a patient who had the Roux-en-Y gastrectomy, which is a reconstructive operation.

First Embodiment

Referring now to FIGS. 1-7, the endoscopic system and the therapeutic procedure according to the first embodiment will now be described.

Figure 1:
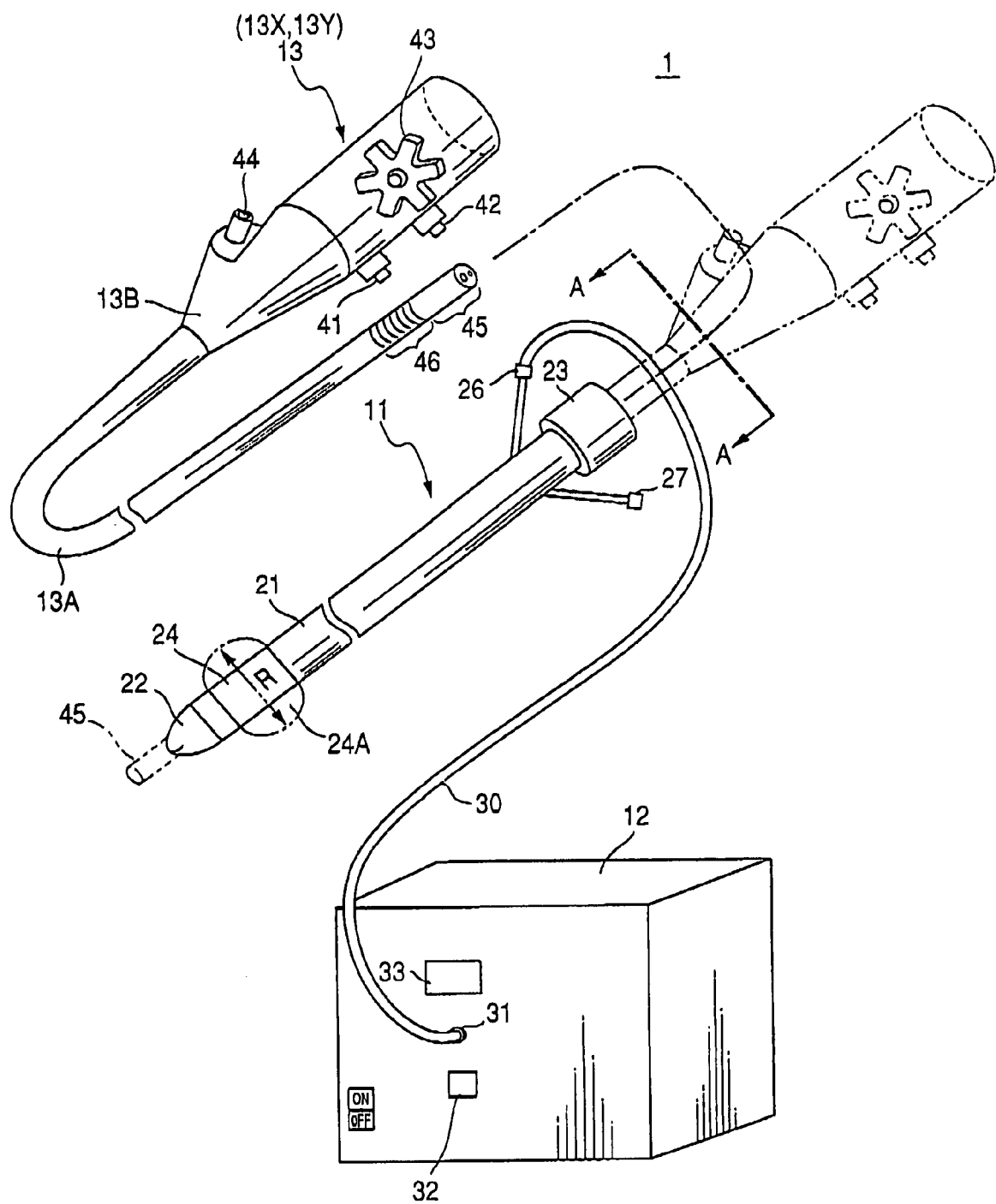
FIG. 1 is a perspective view outlining the configuration of an endoscopic system according to a first embodiment of the present invention.

FIG. 1 shows the configuration of a primary part of the endoscopic system 1. As shown therein, the endoscopic system 1 is equipped with an overtube 11 on which a balloon is loaded, an air-supply device 12 controlling the expansion and shrinkage of the balloon of the overtube 11, and an endoscope 13 to be inserted together with the overtube 11 into body cavities or tubular cavities of an object (for example, the duodenum subjected to oral insertion). The endoscope 13 has an insertion tube inserted into an insertion channel of the overtube 11, and with its inserted state, the endoscope 13 is inserted into a body cavity or a tubular cavity of the object such that the overtube 11 is led.

The overtube 11 is made of a resin material, such as polyurethane, thermoplastic elastomer, fluorinasted resin, or silicon. This overtube 11 is provided with a flexible tubular portion 21 which is formed as a whole into a substantially cylindrical shape and has a bendable characteristic, a distal end portion 22 integrally formed with one end (distal end) of the flexible tubular portion 21, and a grip 23 integrally formed with the other end of the flexible tubular portion 21. In the following, the side going towards the distal end portion 22 is called "distal end side," while the side going towards the grip 23 is called "base end side."

The flexible tubular portion 21 is a cylindrical member in which there is formed an insertion channel P1, into which the insertion tube of the endoscope 13 is inserted. On the outer surface of the flexible tubular portion 21, a balloon 24 is mounted at a predetermined position in a longitudinal direction (hereinafter referred to as an "axial direction") of the flexible tubular portion 21. This balloon 24 is a flexible thin bag member made of resin material (thermoplastic resin made of silicon, latex, polyurethane, or nylon) and air-tightly loaded on the outer surface of the flexible tubular portion 21. Thus the balloon 24 is produced to selectively expand and shrink in response to supplying and discharging air thereto and therefrom. The balloon 24 is therefore expanded to fixedly position the overtube 11 in a body cavity or a tubular cavity of an object to be examined.

The whole body of the flexible tubular portion 21 or at least the distal end portion 22 is made of a material including an X-ray non-transmission substance. Under the X-ray fluoroscopy, the existence of the X-ray non-transmission substance portion can be detected in a distinguishable manner.

Figure 2:
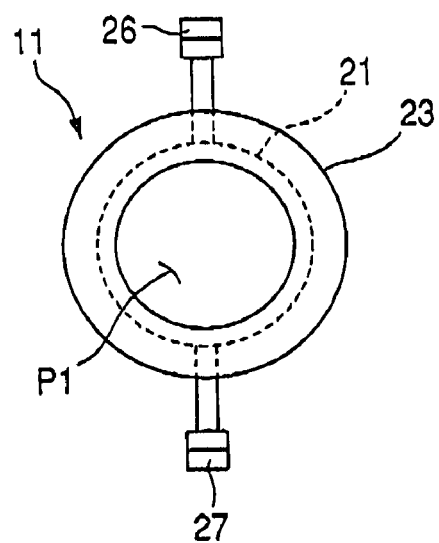
FIG. 2 is a side view taken along an A-A line in FIG. 1.
Figure 3:
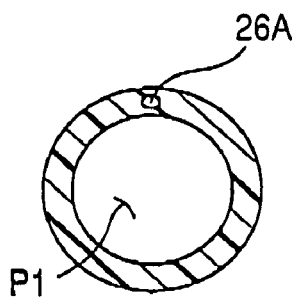
FIG. 3 is a sectional view taken along a B-B line in FIG. 1.
Figure 4:
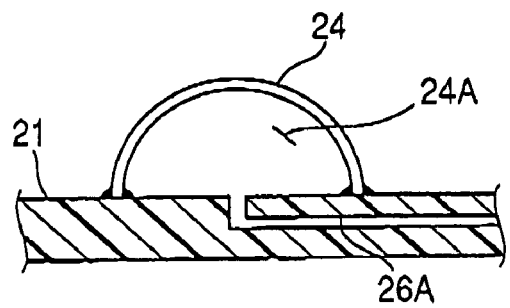
FIG. 4 is a partial sectional view explaining the geometrical relationship between a balloon and an air-supply channel.

In addition, as shown in FIG. 2, on the flexible tubular portion 21, an arm-like air-supply mouth ring 26 and an arm-like water-supply mouth ring 27 are formed. These mouth rings 26 and 27 are protruded from the outer surface of the flexible tubular portion 21 on the base-end side thereof so that the positions of the mouth rings bisect the circumference of the flexible tubular portion.

Of these, the water-supply mouth ring 26 is open from the inner circumferential surface of the flexible tubular portion 21, that is, to the insertion channel P1 which is inside the flexible tubular portion. Hence, water (e.g., normal saline) supplied from a not-shown water-supply source to the water-supply mouth ring 26 is subjected to moistening the inner circumferential surface.

The air-supply mouth ring 27 is made to communicate with an air-supply channel 26A (refer to FIG. 3) produced in the body of the flexible tubular portion 21. This air-supply channel 26A communicates with an inner cavity 24A of the balloon 24 (refer to FIG. 24). The air-supply mouth ring 26 is connected to an air-supply port 31 of the air-supply device 12 via a hose 30. The air-supply device 12 is equipped with an air-charge/discharge switch 32, which is operated to supply, for example, air from the air-supply port 31. Hence when the air is supplied from the air-supply device 12, the supplied air reaches the air-supply mouth ring 26 via the hose 30, and then reaches the inner cavity 24A of the balloon 24 via the air-supply channel 26A, expanding the balloon 24. This expanded state is pictorially illustrated by an imaginary line in FIG. 1. Further, the air-supply device 12 is equipped with a pressure display monitor 33 that represents the pressure of the balloon 24. Alternatively a syringe to charge and discharge air may be used in place of the air-supply device.

The inner cavity of the balloon 24 has a preset volume, which is allowed to expand up to a preset-size balloon in response to supplying air of a predetermined specified volume. The cubic capacity of the expanded balloon Is set to be adapted to different diameters of a target part (i.e., a body cavity or a tubular cavity) to which the balloon is fixed, wherein the different diameters absorb differences of individuals.

Meanwhile when the switch 32 is operated to discharge the air, the air in the balloon 24 is discharged through the path opposite to the above, thus shrinking the balloon 24. The shrunk balloon is pictorially shown by a solid line in FIG. 1. In this shrunk state, the balloon 24 is touched as a whole to the outer circumferential surface of the flexible tubular portion 21 so as to be almost flat thereon.

In the present embodiment, the shape and size of the balloon 24 are decided such that the balloon 24 comes into contact with the inner walls of each of the duodenum and the jejunum when a predetermined amount of air is supplied into the balloon. The shape is defined by a diameter R (diameter including the diameter of the flexible tubular portion 21) and an axial length L of the balloon most expanded.

The endoscope 13 is provided with an elongated insertion tube 13A which is flexible and an at-hand operation device 13B formed integrally with the base end of the insertion tube 13A. The at-hand operation device 13B is provided with various types of switches 41 and 42 for use in air supply and water supply, an operation lever 43 for use in bending the insertion tube 13A, a forceps cap 44 through which a therapeutic forceps (not shown) is inserted into the insertion tube 13A. A distal end, having a specified axial length, of the insertion tube 13A is rigid and formed as a distal end portion 45 and a CCD camera and a lighting source (both not shown) are embedded in the distal end portion 45. Further, the insertion tube 13A has a bendable portion 46 positioned next to the distal end portion 45. The bendable portion 46 operates to respond to wires which go forward and backward selectively in response to operator's operations at the operation lever 43, so that, for example, the insertion tube 13A is bendable selectively in the upward, downward, rightward and leftward directions defined when being viewed along the axial direction of the insertion tube.

In the present embodiment, the endoscope 13 is either a first endoscope 13X or a second endoscope 13Y, which is used depending on purposes. The first endoscope 13X is either a forward-viewing endoscope or an oblique-viewing endoscope and the second endoscope 13Y is a side-viewing endoscope. For generally indicating the endoscopes, a reference numeral "13" is simply used, and for distinguishably indicating "forward viewing" or "oblique viewing" and "side viewing," reference numerals "13X" and "13Y" are used selectively. The "forward viewing" is viewing a forehand view along the axial direction of the insertion tube of an endoscope, the "side viewing" is viewing in a direction substantially perpendicular to the foregoing axial direction, and the "oblique viewing" is viewing in angles between the forward and side viewing directions.

(Treatment Technique Including Approach to Vater's Papilla)

A treatment technique that uses the endoscope system according the present embodiment, which includes an approach to the Vater's papilla of a patient (i.e., an object being treated), will now be described.

Prior to describing a practical treatment technique, a Roux-en-Y gastrectomy will now be explained briefly. This Roux-en-Y Gastrectomy is one of the reconstructive techniques used after totally or partly resecting the stomach. In the Roux-en-Y reconstructive operation, the most part of the stomach or a part of the esophagus, which is adjacent to the cardia of the stomach, and a part of the duodenum, which is adjacent to the pylorus of the stomach, are resected. The stump of the duodenum is sealed. The jejunum connected to the duodenum fixed in the abdominal cavity by the ligament of Treitz is cut at a lower position of the ligament of Treitz. The anus-side jejunum divided by this cut portion is anastomosed (or inosculated) with the remaining stomach or the esophagus. In addition, the jejunum connected with the duodenum, which is connected with the pancreas and the gallbladder, is anastomosed with the jejunum anastomosed with the remaining stomach or the esophagus.

Figure 5:
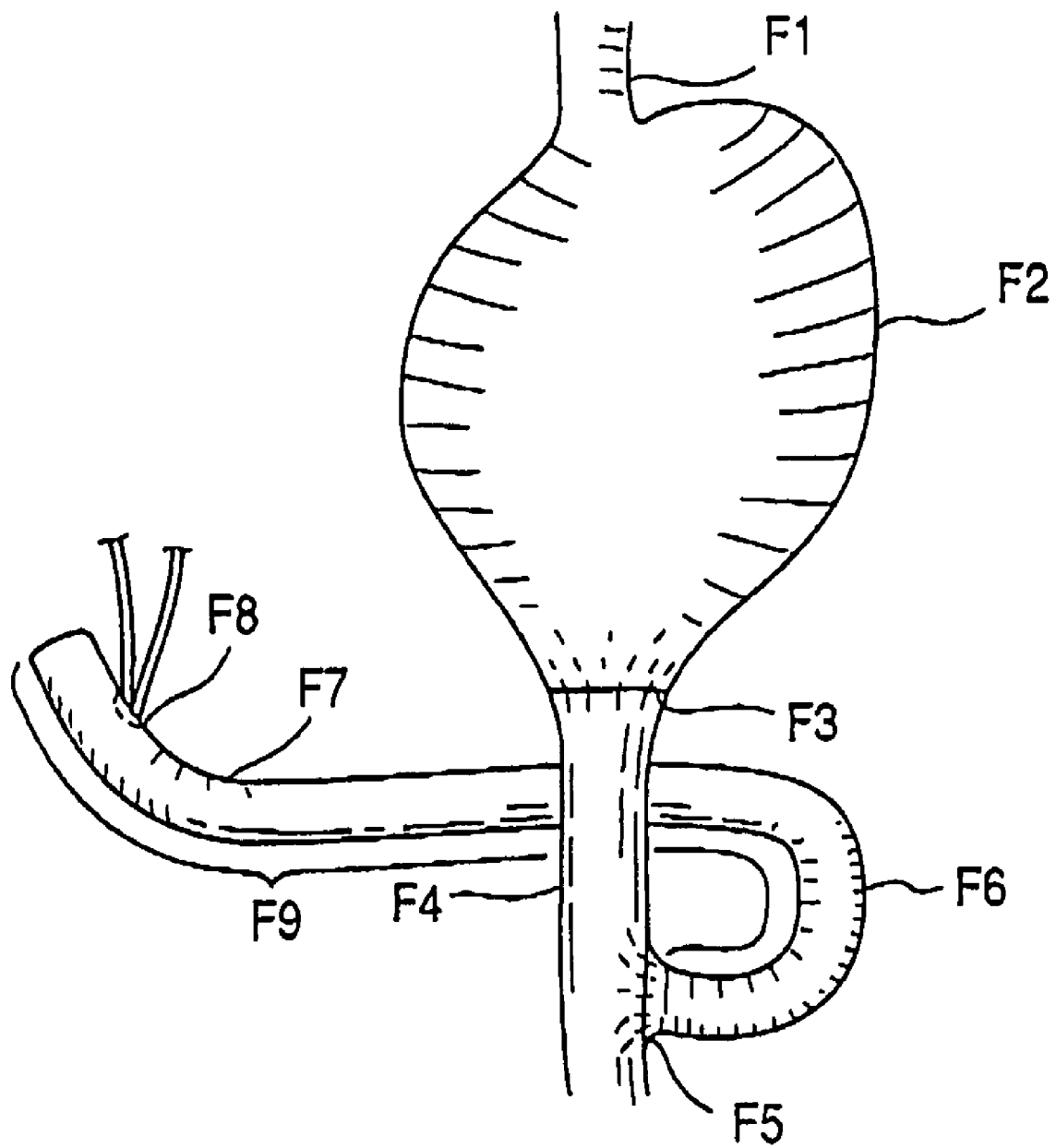
FIG. 5 explains a path from the stomach of a patient who had a Roux-en-Y reconstructive operation to the Vater's papilla thereof.

That is, as shown in FIG. 5, the jejunum F4 is connected with the remaining stomach F2 via a stomach-to-jejunum anastomosed portion F3 and also the jejunum F4 is connected with the duodenum F7 via a jejunum-to-jejunum anastomosed portion F5 and a jejunum-anastomosed bent portion F6. In general the jejunum-anastomosed bent portion F6 is characteristic of being narrower. Additionally, a part ranging from the jejunum-to-jejunum anastomosed portion F5 to the stump of the duodenum via the jejunum-anastomosed bent portion F6 and the Vater's papilla F8 is called an afferent loop F9. One of the characteristics of the Roux-en-Y reconstruction is that the afferent loop F9 is longer.

Thus, when an endoscopic treatment of pancreatic duct and biliary duct is performed with a Roux-en-Y gastrectomy patient, it is necessary that the thin and long insertion tube of an endoscope is orally inserted the esophagus Ft of the patient such that the insertion tube pass the stomach F2 and is inserted into the afferent loop F9 via the jejunum-to-jejunum anastomosed portion F5. And it is necessary that the insertion tube should advance retrogradely in the afferent loop F9.

In the present embodiment, the treatment technique that considers those circumstances is provided, which will now be detailed with referenced to FIGS. 6-11, with focusing an approach to the Vater's papilla.

(Approach to Vater's Papilla (Approach Procedure))

First a doctor inserts the insertion tube 13A of the first endoscope 13X into the insertion channel P1 of the overtube 11. At this stage, the balloon 24 is in its shrunk state. Before this insertion, water is supplied from the overtube 11 or the water-supply port 27 via the water-supply mouth ring 27 of the overtube 11 or a not-shown water-supply channel through the distal end of the insertion tube 13A of the first endoscope 13X, so that the wall surface of the insertion channel P1 is moistened. Hence the passing performance for inserting and pulling the insertion tube 13A through the insertion channel Pt improves, providing an improved operability. After this water supply, the insertion tube 13A is inserted into the insertion channel P1, and the distal end portion 45 of the insertion tube 13A is made to slightly protrude from the distal end portion 22 of the overtube 11 (refer to a dashed-two dotted line depicted in FIG. 1). This provides a field of view to a CCD camera of the insertion tube 13A.

Figure 6:
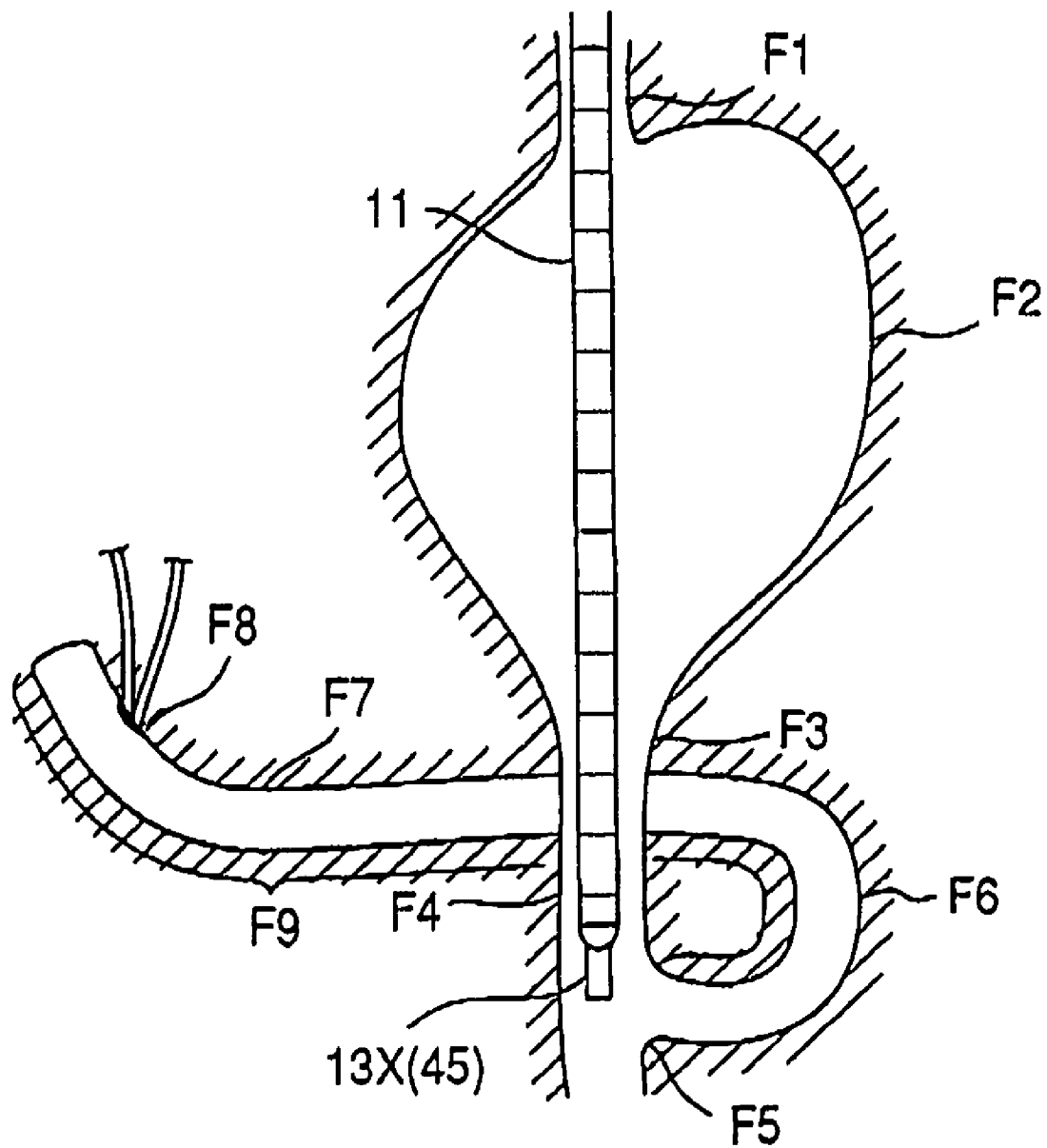
FIGS. 6-12 explain, respectively, how to approach the Vater's papilla in the first embodiment.

In this inserted state, as shown in FIG. 6, as observing forward-viewing images from the first endoscope 13X, the doctor orally inserts, via the esophagus F1 and the stomach F2, both the overtube 11 and the insertion tube 13A of the first endoscope 13X into the jejunum F4. And, as shown in FIG. 6, when the distal end portion 45 of the insertion tube 13 reaches a position adjacent to the jejunum-to-jejunum anastomosed portion F5, the insertion is temporarily stopped. An alternative insertion way is that, with the overtube kept on the at-hand portion of the first endoscope 13X, the first endoscope 13X is first inserted into the jejunum F4, and then the overtube 11 is made to advance forward.

Figure 7:
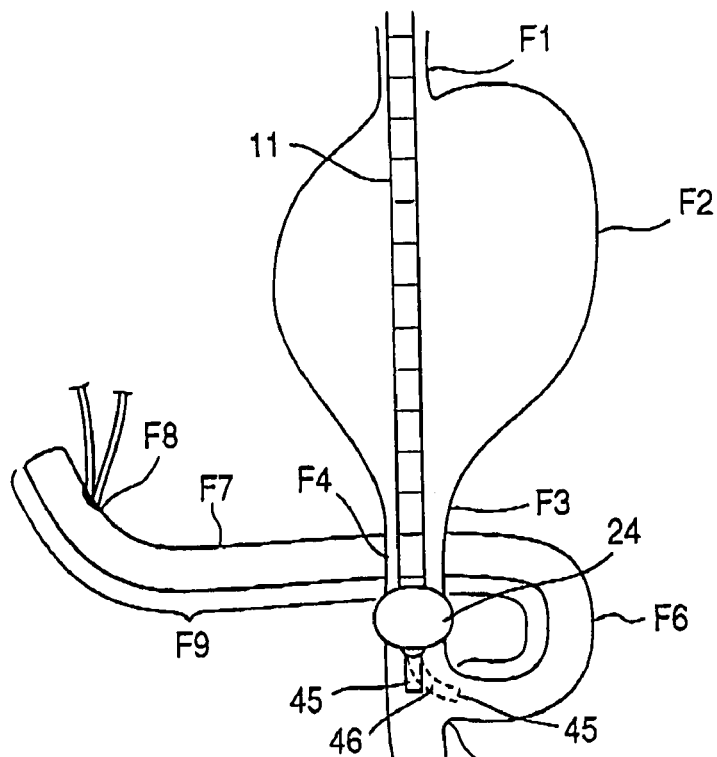
Figure 8:
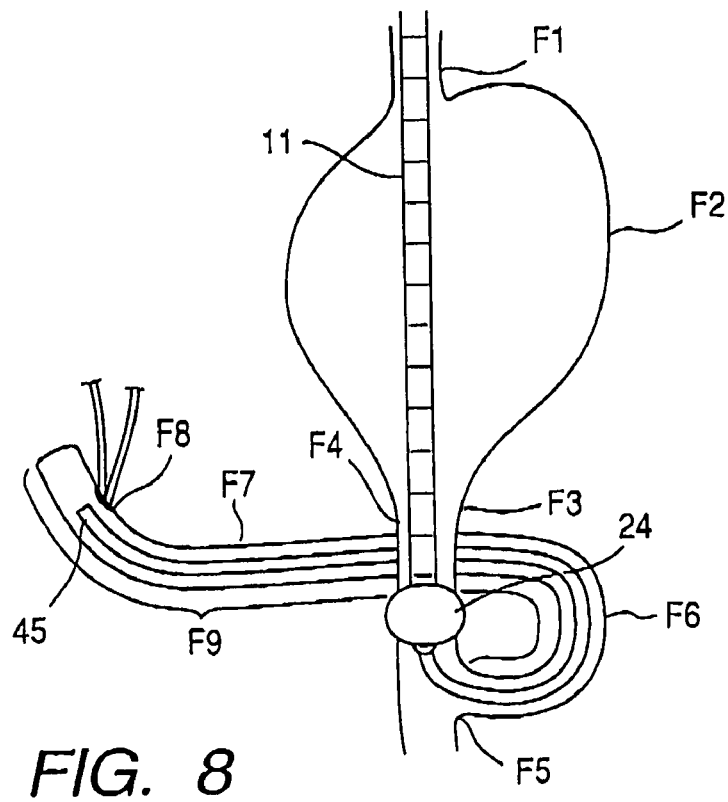

Then, as shown in FIG. 7, the doctor operates the switch 32 of the air-supply device 12 to supply a predetermined amount of fluid (air in the embodiment) to the balloon 24 of the overtube 11. Responsively to this air supply, the balloon 24 expands to have a predetermined inner cavity volume, where the outer surface thereof is forced to partially touch the wall surface of the jejunum F4 in a tight manner. As a result, the balloon 24, i.e., overtube 11 is positionally fixed to the jejunum F4. In this positionally fixed state, the distal end of the insertion tube 13A of the first endoscope 13X, that is, the distal end portion 45 tracks in its view the jejunum-to-jejunum anastomosed portion F5.

When the above state is established, the doctor operates the operation lever 43, which is equipped at the at-hand operation device 13B of the first endoscope 13X, in such a manner that the bendable portion 46 is bent to enable the distal end portion 45 of the insertion tube 13A to be directed toward the jejunum-to-jejunum anastomosed portion F5. This situation is illustrated by a two-dotted dashed line in FIG. 7. Specifically, this bending operation becomes a subtle guide operation necessary to smoothly feed the insertion tube 13A into the jejunum-to-jejunum anastomosed portion F5 which is opened almost perpendicularly to the jejunum F4. During this guide operation, both the bendable portion 46 and the distal end portion 45 are bent with the use of the balloon 24 of the overtube 11 as a fulcrum. This fulcrum is positionally fixed to the jejunum F4, so that the bending operation is unlikely to have influence of peristalsis of the jejunum and/or the stomach, gaining steadiness and stableness in the bending operation. This guide operation surely positions the insertion tube 13A at the inlet of the afferent loop.

Though the jejunum-to-jejunum anastomosed portion F5, which is the inlet of the afferent loop F9, is narrower, the insertion tube 13A can easily be inserted into the afferent loop F9 with the aid of the positional fixing function given by the balloon 24.

After the guide operation, in a state where the overtube 11 kept there as it is, the doctor manually operates the insertion tube 13B so that the insertion tube is fed into the afferent loop F9. This insertion is a feeding operation carried out after the positioning operation by which the distal end portion of the insertion tube 13B, that is, the distal end portion 45, is already positioned to slightly intrude into the jejunum-to-jejunum anastomosed portion F5, that is, the afferent loop F9. Accordingly, the insertion tube 13A smoothly passes from the jejunum-to-jejunum anastomosed portion F5 to the jejunum-anastomosed bent portion F6 in response to operations at the insertion tube.

The foregoing feeding operations allow the insertion tube 13A of the first endoscope 13X to be penetrated into a deeper part in the afferent loop F9. Since the first endoscope 13X is either a forward-viewing endoscope or an oblique-viewing endoscope, endoscopic images presented on the monitor are able to the Vater's papilla F5 which is located on and in the wall of the duodenum F7. Accordingly, with tracking the tubular cavity of the duodenum in the endoscopic images, the Vater's papilla F8 can be searched, whereby the Vater's papilla can be found easily. When the distal end portion 45 arrives at a neighboring position with the Vater's papilla F8, the doctor stops to insert the insertion tube 13A any more, where the first endoscope 13X is kept there.

Figure 9:
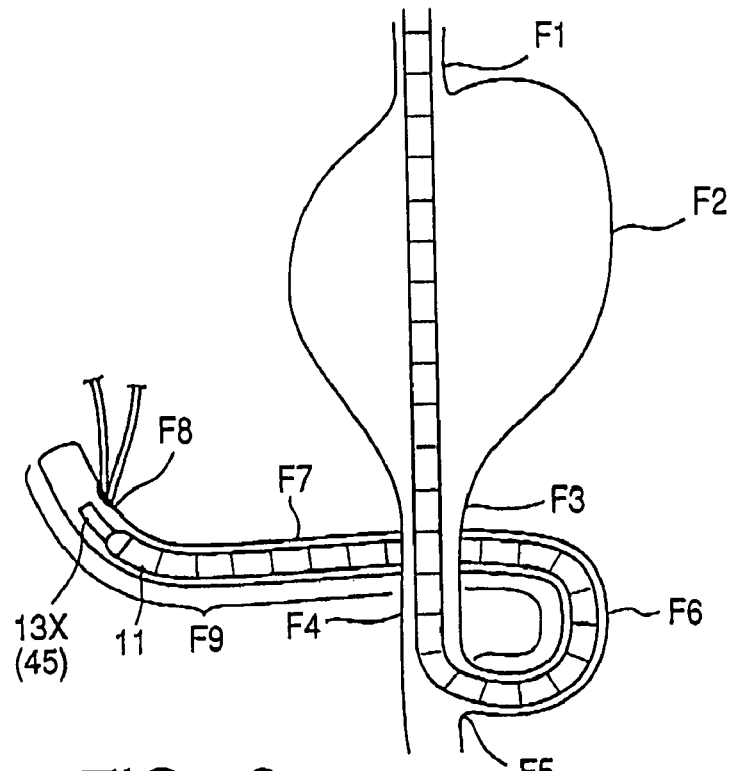

Then the doctor operates the switch 32 of the air-supply device 12 to have the balloon 24 attached on the overtube 11 shrunk, and inserts the overtube 11 into the afferent loop F9 along the insertion tube 13A of the first endoscope 13X. This makes it possible to make the distal end of the overtube 11 arrive at a position neighboring the Vater's papilla F9, as shown in FIG. 9.

Figure 10:
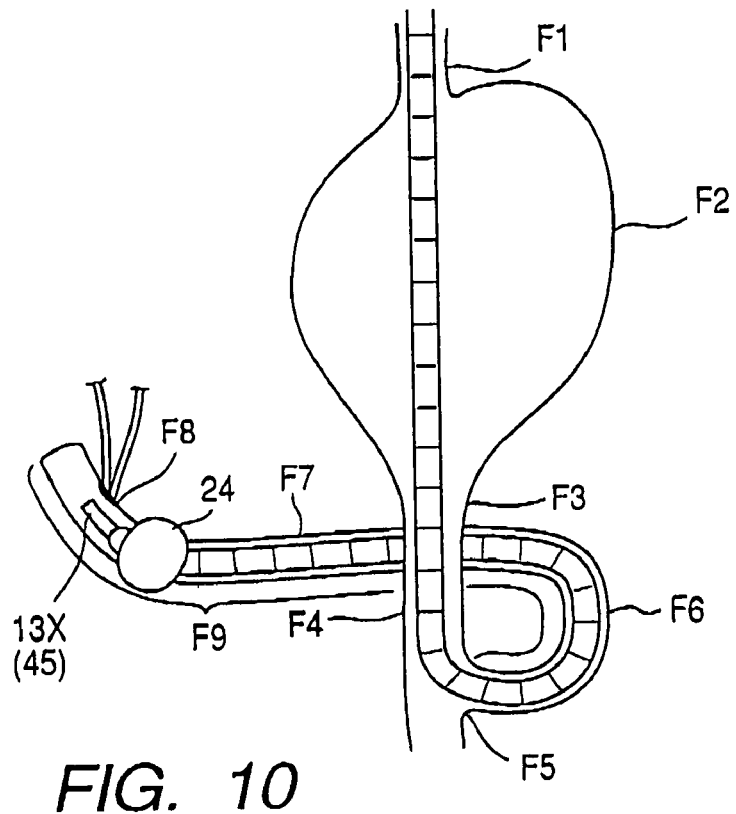
Figure 11:
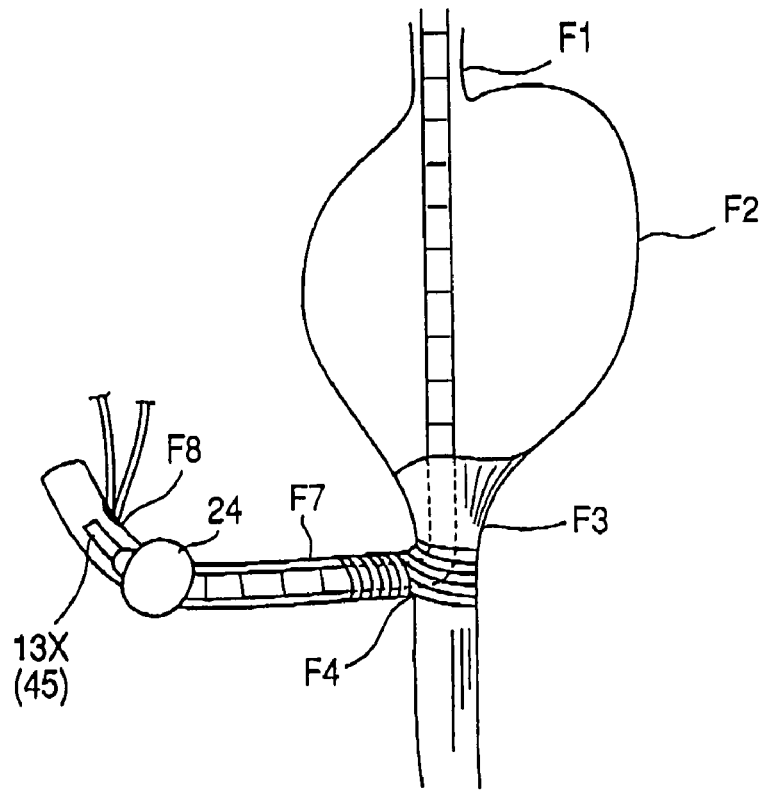

After this, the doctor operates to expand again the balloon 24 on the overtube 11, as shown in FIG. 10. Hence the balloon 24 is able to tightly adhere to the wall of the duodenum F7 at a position before the Vater's papilla F8, so that the balloon 24, i.e., overtube 11 is positionally fixed to the duodenum F7. As illustrated in FIG. 11, the doctor pulls both the overtube 11 and the first endoscope 13X at the same time to try to shorten the jejunum F4, jejunum-to-jejunum anastomosed portion F5, and duodenum F7. This causes the overtube 11 and the first endoscope 13X to be straight except their bendable portions. FIG. 11 shows the jejunum which is made shortened and straight.

Figure 12:
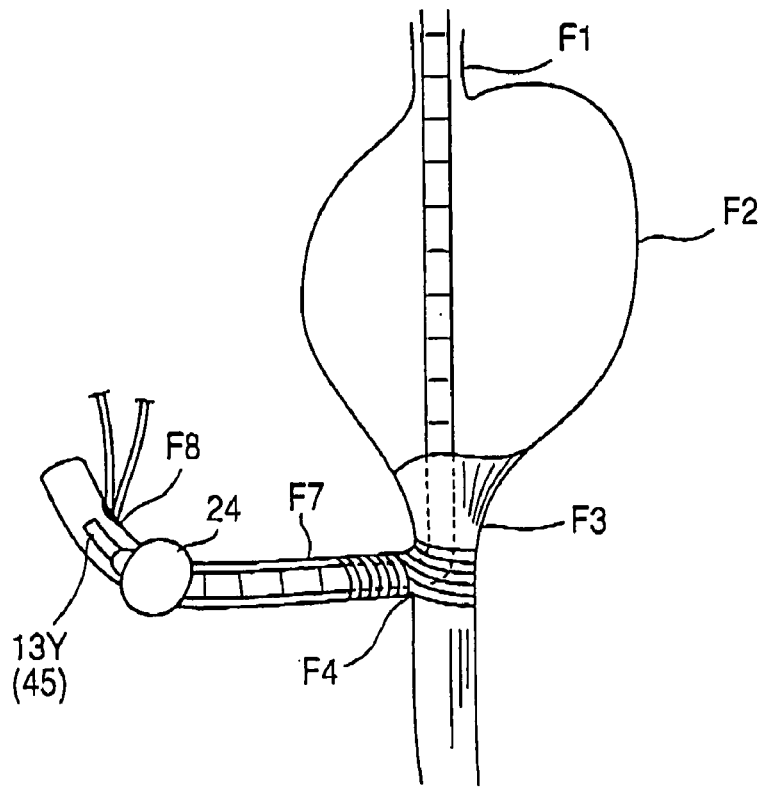

The doctor then pulls back the first endoscope 13X from the overtube 11. Then, using the water-supply port 27 of the overtube 11 which has been orally inserted and kept in the body, water is supplied into the insertion channel P1. This water supply facilitates the insertion of a second endoscope 13Y which will then be used. Together with this water supply, the doctor inserts the second endoscope 13Y into the insertion channel P1 of the overtube 11. It is preferred that water is supplied into the insertion channel P1 from even the second endoscope 13Y during the insertion of the second endoscope. The second endoscope 13Y is a side-viewing endoscope. As shown in FIG. 12, the second endoscope 13Y is guided by the overtube 11, so that the second endoscope can easily reach a position adjacent to the Vater's papilla F8.

The second endoscope 13Y provides side-viewing images of the Vater's papilla F8. Using those side-viewing images, the doctor engages in endoscopic diagnosis and, if required, inserts a therapeutic instrument through the forceps cap 44 to use the instrument for therapeutic treatments such as a treatment of pancreatic duct and biliary duct.

The second endoscope 13Y is a side-viewing endoscope equipped with an elevating device in its distal end portion 45, which elevating device is for elevating a therapeutic instrument. Both the bendable portion 46 and the distal end portion 45 of the second endoscope 13Y are operated on the fixed positions of the balloon 24 of the overtube 11, where the fixed positions serve as a fulcrum. Thus the diagnosis and treatments can be made easier.

In this way, according to the endoscopic system 1 according to the present embodiment, the two types of endoscopes 13X and 13Y, which are a forward- or oblique-viewing type and a side-viewing type, can be used for purposes. Specifically, for the approach to the Vater's papilla F8, the first endoscope 13X is used dedicatedly, in which forward images along the advancing direction are subjected to doctor's observation in inserting the overtube 11. Namely, the advantage of the forward- or oblique-viewing images can be utilized for approaching to the Vater's papilla F8, which is easier for doctors in carrying out the approaching procedure. When diagnosis and necessary treatments are performed with the Vater's papilla F8, the second endoscope 13Y is used under side-viewing images, making the treatments easier.

In the former approach, the balloon 24 provides the positional fixing function between the overtube and the jejunum F4 at the position before and adjacent to the jejunum-to-jejunum anastomosed portion F5. Thanks to this positional fixing function, when the insertion tube 13A of the first endoscope 13X is bent laterally toward the inlet of the afferent loop (i.e., the jejunum-to-jejunum anastomosed portion F5), this directional change can be done in a stable and reliable manner. In other words, since the overtube 11 is positionally fixed within the body, the insertion tube 13A of the endoscope 13X resists the influence caused by motions of organs including the jejunum. Hence the operator's operations can be a simple bending operation by which the distal end portion of the insertion tube 13A is bent by a necessary amount of bending angle. For doctors, the operations at the operation lever 43 can be reflected directly in changing the directions, facilitating the operations for directional changes toward the afferent loop F9.

In addition, by using the insertion tube 13A of the first endoscope 13X as a lead, the overtube 11 is then fed along the insertion tube 13A. Hence feeding the overtube 11 can be facilitated.

Further, when the distal end of the overtube 11 is located at the Vater's papilla F8, the balloon 26 is expanded again, thereby allowing the distal end of the overtube 11 to be fixed positionally relative to the duodenum F7. It is therefore prevented that organic motions result in changing the position of the overtube 11 and falling off the overtube 11. In a state where the distal end is positionally fixed in this way, the endoscope is replaced by a side-viewing type endoscope. This change in the types of the endoscopes can be facilitated and smoothed, owing to the fact that the jejunum F4, jejunum-anastomosed bent portion F6, and duodenum F7 are already piled up by the overtube 11 to be straight in order to secure an insertion route for the next endoscope and the insertion route is positionally fixed by the balloon 24.

Accordingly, for patients who have the Roux-en-Y reconstructive operation, the access to the Vater's papilla F8 can be made speedier, more stable and easier after, as much as possible, smoothly passing the jejunum-to-jejunum anastomosed portion F5 and the jejunum-anastomosed bend portion F6.

Incidentally, the insertion tube of the first endoscope 13X may have a function to change the hardness thereof. This function enhances the guide performance which is for feeding the overtube 11 into the afferent loop F9 deeply along the insertion tube 13A, making the feeding operations easier.

Moreover, according to need, it is possible to pass over the position fixing step carried out at the jejunum by expanding the balloon on the overtube 11, which step is shown in FIG. 7.

Second Embodiment

Figure 13:
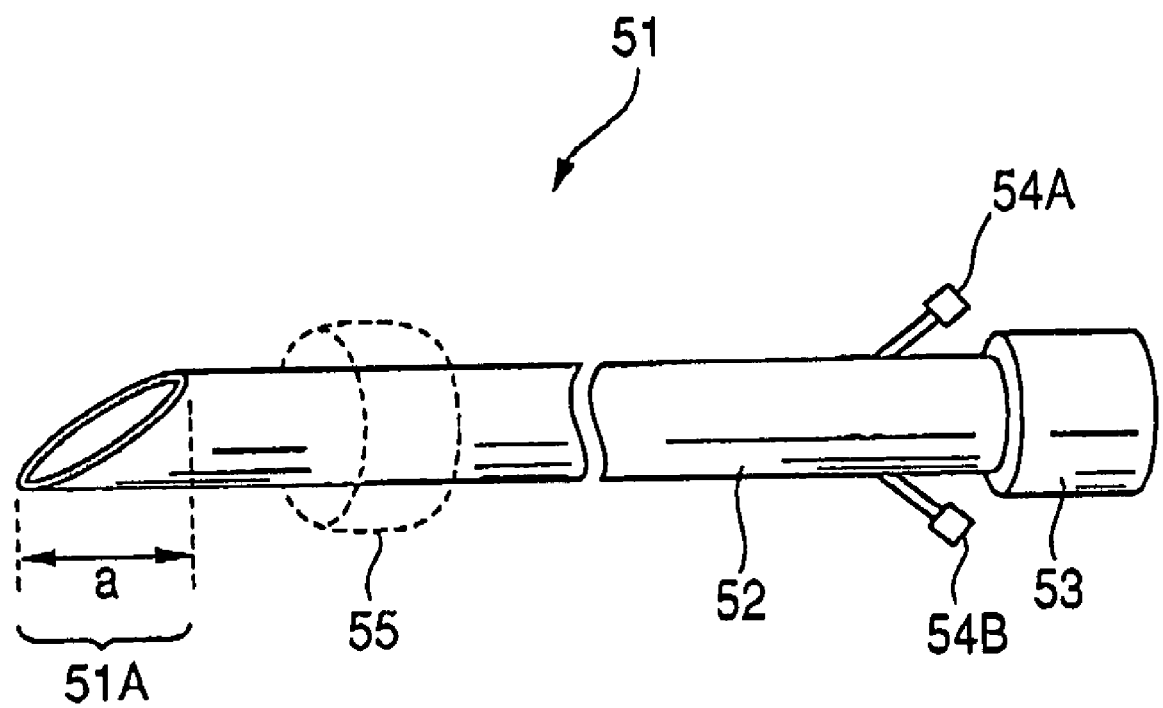
FIG. 13 is a partial perspective view showing an overtube employed by an endoscopic system according to a second embodiment of the present invention.
Figure 14:
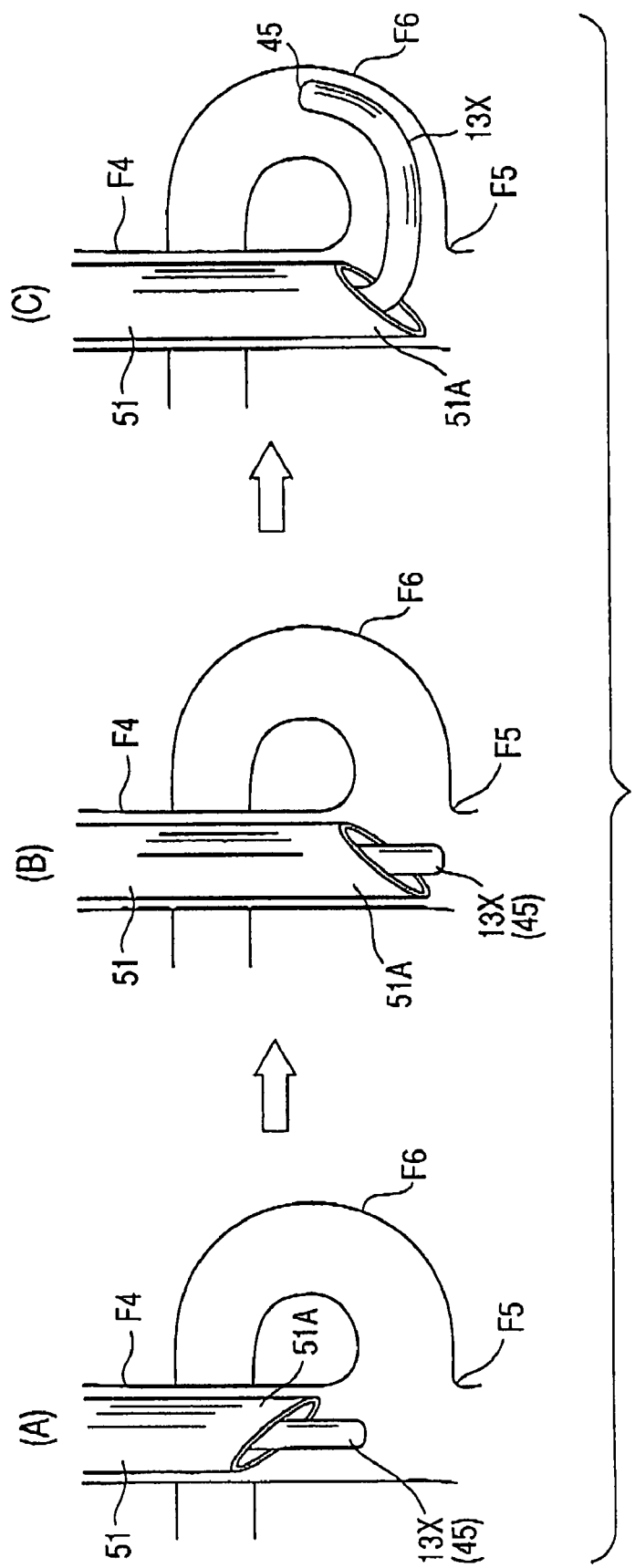
FIG. 14 explains part of the processes to approach the Vater's papilla in the second embodiment.

Referring to FIGS. 13-14, a second embodiment of the endoscopic system according to the present embodiment will now be described.

Similarly to that in the first embodiment, an overtube 51 shown in FIG. 13 is provided with a flexible tubular portion 52 being made of resin and having flexibility, a grip 53 formed integrally with an at-hand side portion of the flexible tubular portion 52, and an air-supply mouth ring 54A and a water-supply mouth ring 54B both formed on the flexible tubular portion 52. Further, the flexible tubular portion 52 has a distal end portion which is obliquely cut over a predetermined length "a" in the axial direction of the distal end portion, which distal end portion is provided as a distal end portion 51A having an oblique opening. On the overtube 51, a balloon 55 made similarly to the foregoing one is loaded at a predetermined position shifted from the distal end portion 51A toward the at-hand side.

An operator inserts the first endoscope 13X into the insertion channel of the overtube 51 and the first endoscope with the overtube is orally inserted into the jejunum F4 of an object being examined. When the images from the first endoscope 13X captures the jejunum-to-jejunum anastomosed portion F5 and the distal end portion 51A of the overtube 51 reaches a position which is short of the jejunum-to-jejunum anastomosed portion F5, the operator manually rotates the overtube 51 on its axis direction from a current unspecified angular position (refer to FIG. 14(A)) to an angular position at which the oblique opening of the distal end portion 51A is oriented toward the jejunum-to-jejunum anastomosed portion F5 (refer to FIG. 14(B)).

This rotational operation may be performed with the use of a marker (not shown) applied on the grip 53 of the overtube 51 or the contour of the distal end portion 51A captured in X-ray transmitted images when X-ray fluoroscopy is accompanied, as in ERCP.

After the rotational operation, the operator bends the insertion tube 13A of the first endoscope 13X so that its distal end portion 45 is protruded from the oblique opening of the distal end portion 51A, which is now directed toward the jejunum-to-jejunum anastomosed portion F5, and oriented toward the jejunum-to-jejunum anastomosed portion F5. And, as shown in FIG. 14(C), while the insertion tube 13A is pushed forward with the oriented attitude so that the insertion tube 13A is inserted into the afferent loop F9 beginning from the jejunum-to-jejunum anastomosed portion F5. The other steps in approaching to the Vater's papilla F8 are similar or identical to those in the first embodiment.

In this way, when the oblique opening is directed toward the jejunum-to-jejunum anastomosed portion F5, the insertion tube 13A of the first endoscope 13X can be bent in a state where the distal end of the overtube 51 is located closer to the anastomosed portion F5. Thus the overtube 51 is given a more effective positional fixing function, so that the overtube 51 can be inserted more smoothly under easier operations. Additionally, in the present embodiment, since the overtube 51 is subjected to the rotational operations, it is easier that the insertion tube 13A of the first endoscope 13X be guided into the afferent loop F9 even when the positional fixing function given by the balloon 55 is not utilized. Like the first embodiment, it is thus possible to allow the insertion tube 13A to pass through the thin and long afferent loop F9. As a result, the present embodiment can provide the similar operations and advantages to those explained in the first embodiment.

Of course, the insertion tube 13A of the first endoscope 13X may be bent and inserted into the afferent loop F9 with the parallel use of the positional fixing function of the balloon 55 to the jejunum F4.

The foregoing configuration described in the second embodiment can be reduced into practice in further various modified modes. Those modifications will be exemplified below, in which the same or identical configurations to those in the first or second embodiments, or other modifications are given the same reference numerals, with the description thereof omitted or simplified.

(First Modification)

Figure 15:
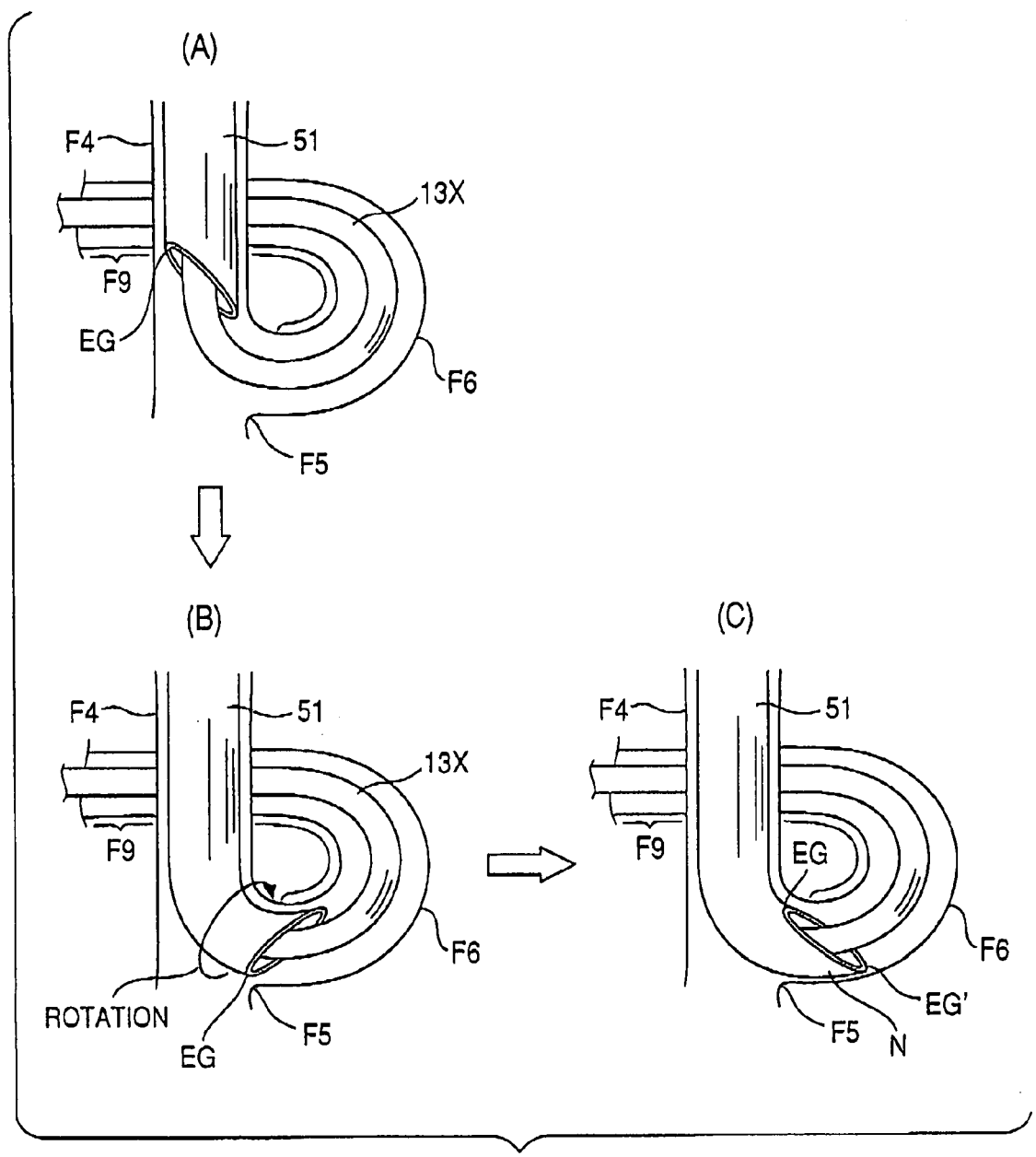
FIG. 15 explains part of the processes to approach the Vater's papilla in a first modification.

FIG. 15 shows a first modification, which is concerned with an example showing how to operate the foregoing overtube 51.

In the foregoing second embodiment, the overtube 51 is inserted into the afferent loop F9 with the use of, as a guide, the insertion tube 13A of the first endoscope 13X. For this insertion, under X-ray fluoroscopy, an operator inserts the overtube 51 into the jejunum F4 (FIG. 15(A)), and rotates the overtube 51 in such a manner that an edge EG' of the distal end portion 51A (i.e., the distal-end-side edge of the oblique opening) is oriented toward the jejunum-to-jejunum anastomosed portion F5 (FIG. 15(B)). And, as shown in FIG. 15(B), when the opposite-side edge EG of the distal end portion 51A (i.e., the at-hand-side edge of the oblique opening) enters the inlet of the jejunum-to-jejunum anastomosed portion F5, the overtube 51 is rotated by 180 degrees on its axial direction. Thus, as shown in FIG. 15(C), the distal-end-side edge EG', which faces the edge EG, is located on the outer-circumferential wall side inside the afferent loop F9. Accordingly, the edge EG' of the distal end portion 51A touches a lower side part N of the jejunum-to-jejunum anastomosed portion F5, so that the overtube 51 can be pushed forward with the use of the edge EG' as a fulcrum, enabling the overtube 51 to be inserted more easily along the afferent loop F9. Additionally, since the distal-end-side edge EG' receives a support from the jejunum-to-jejunum anastomosed portion F5, the overtube 51 can be inserted in an uneasy-to-be pulled manner.

(Second Modification)

Figure 16:
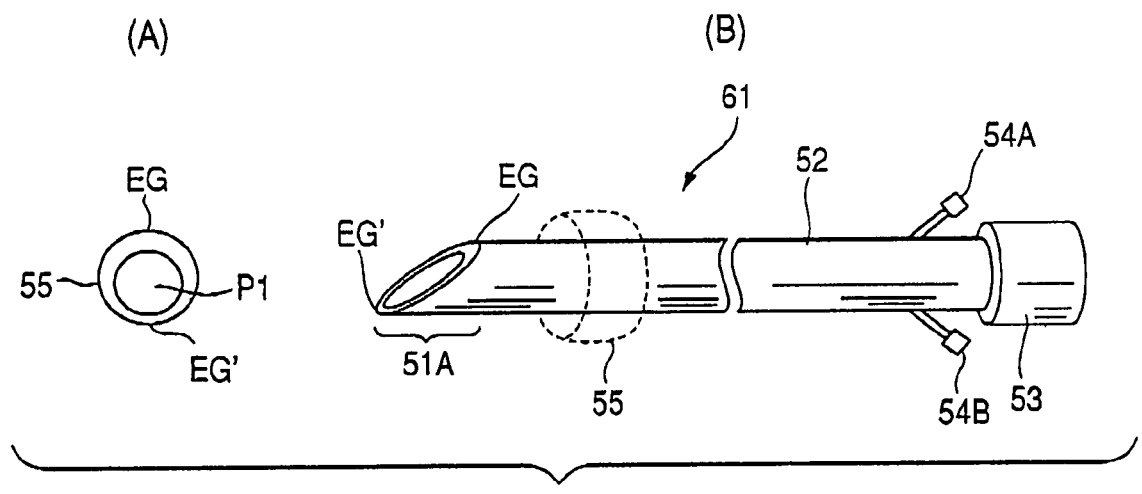
FIG. 16 is a partial perspective view showing an overtube according to a second modification.

FIG. 16 shows a second modification, which concerns another structure of the foregoing overtube 51.

An overtube 61 shown in FIG. 16 is similar in structure to the overtube 51 descried, except that the flexible tubular portion 52 is subjected to uneven thickness formation (refer to FIG. 16(A)). Practically, as the position approaches to the at-hand-side edge EG of the distal end portion 51A with the oblique opening, the thickness of the tube becomes larger. Thus, besides the operations and advantages obtained by the foregoing second embodiment, when the overtube 51 is inserted in the direction shown in FIG. 16(B), the overtube 51 is given an improved resistance against buckling performance.

(Third Modification)

Figure 17:
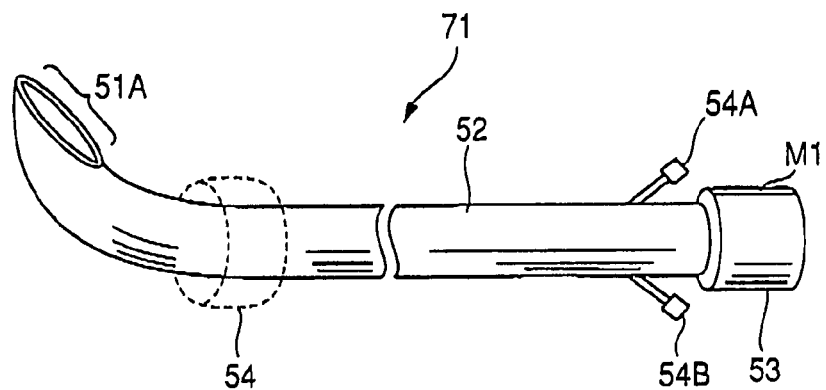
FIG. 17 is a partial perspective view showing an overtube according to a third modification.

FIG. 17 shows a third modification, which also concerns another structure of the foregoing overtube 51.

As shown in FIG. 17, an overtube 71 is similar in structure to the overtube 51 descried, except that its distal end part including the distal end portion 51A is bent previously. Thus the distal end of the overtube 71 is directed inward positively, facilitating the insertion of the overtube 71 into the afferent loop F9. In addition, a marker M1 that indicates the bent direction is put on the grip 53, which provides the overtube 71 with a more facilitated insertion into the afferent loop F9, on top of the operations and advantages similar to those in the second embodiment.

(Fourth Modification)

Figure 18:
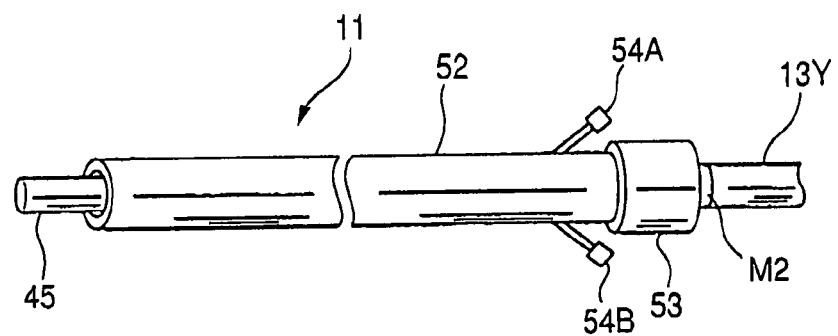
FIG. 18 is a partial perspective view showing a second endoscope inserted in an overtube according to a fourth modification.

FIG. 18 shows a fourth modification, which concerns another example of the second endoscope 13Y.

As shown in FIG. 18, on the at-hand-side outer surface of the insertion tube 13A of the second endoscope 13Y, a marker M2 is put, which is used by an operator to know an amount of protrusion of the distal end portion 45 of the insertion tube 13A which is protruded from the distal end of the overtube 11 by an operator. The overtube applied to this modification may be the one employed in the second embodiment and its modifications.

Thus, besides the operations and advantages similar to those in the first and second embodiments, the present modification has a merit that it is made clearer that how much the second endoscope 13Y should be inserted into the overtube 11 for a treatment of pancreatic and biliary ducts or other treatments, i.e., a target amount for the insertion is shown clearer, making the insertion easier.

(Fifth Modification)

Figure 19:
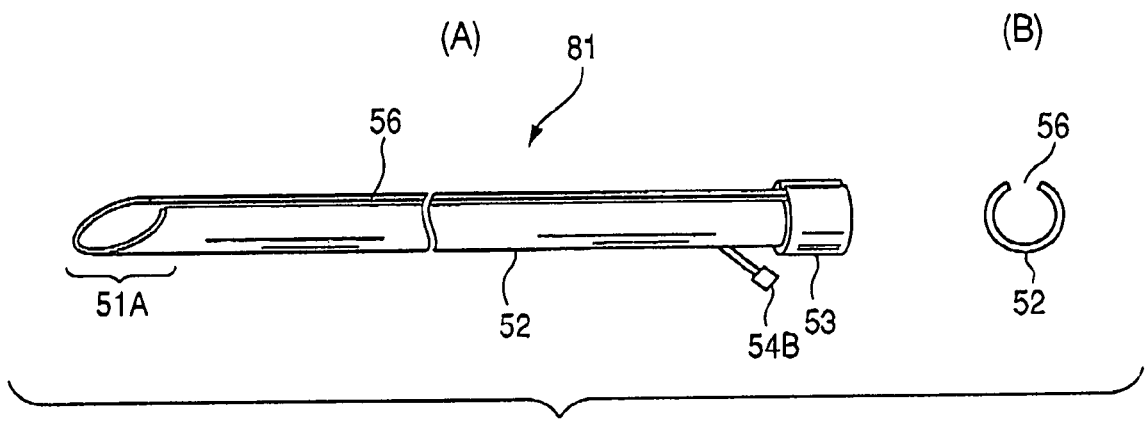
FIG. 19 is a partial perspective view showing an overtube according to a fifth modification.

FIG. 19 shows a fifth modification, which concerns another structure of the overtube.

An overtube 81 shown in FIG. 19(A) has not only the same structure as that of the overtube 51 shown in FIG. 12 but also a slit 56 along an axial area ranging from the flexible tubular portion 52 to the grip 53 (refer to FIG. 19(B)). Incidentally this overtube 81 has no balloon.

In this modification, for inserting the first endoscope 13X into the overtube 81, it is possible that the endoscope 13X is loaded in the overtube 81 from its side, not from the distal end of the endoscope 13X. Accordingly, the insertion (loading) can be made easier.

(Sixth Modification)

Figure 20:
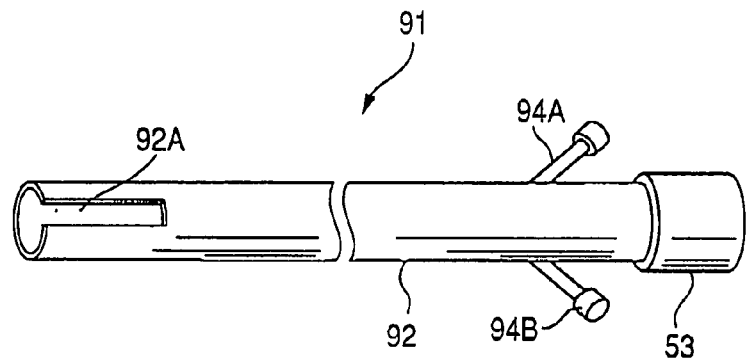
FIG. 20 is a partial perspective view showing an overtube according to a sixth modification.
Figure 21:
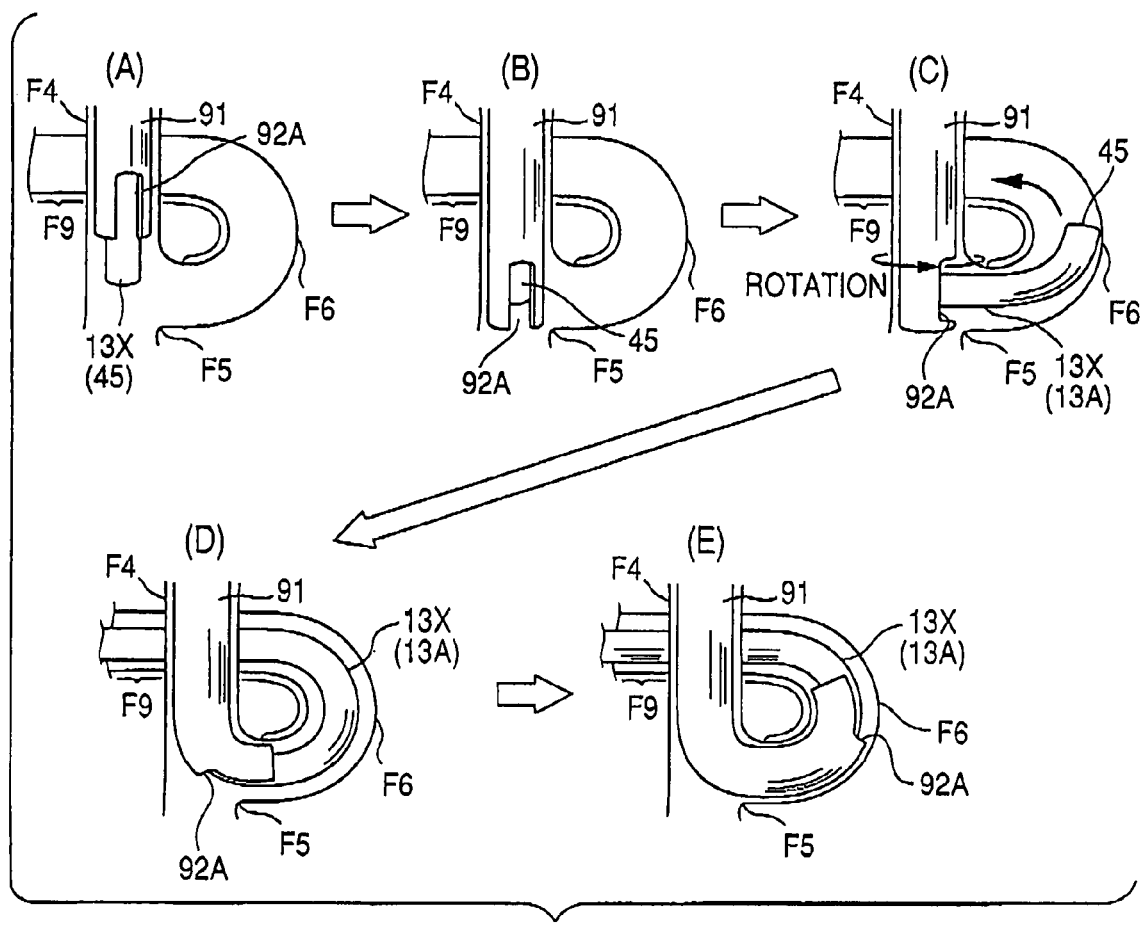
FIG. 21 explains part of the processes to approach the Vater's papilla according to the sixth modification.

FIGS. 20 and 21 show a sixth modification, which still concerns another structure of the overtube.

An overtube 91 shown in FIG. 20 comprises a flexible tubular portion 92 made of resin material and having flexibility, a grip 93 formed integrally with an at-hand-side end of this flexible tubular portion 92, and an air-supply mouth ring 94A and a water-supply mouth ring 94B both formed from the flexible tubular portion 92. Furthermore, through a side wall residing in a distal end part of the flexible tubular portion 92, a slit-shaped side opening 92A with a predetermined length is opened along its axial direction. Incidentally it is not always necessary to load a balloon on this overtube 91.

Thanks to the structure above, the operation for inserting the first endoscope 13X into the afferent loop F9 can be made easier. Specifically, as shown in FIG. 21(A), the overtube 91 is positioned at a position adjacent to the jejunum-to-jejunum anastomosed portion F5 under images the first endoscope 13X. Then, as shown in FIG. 21(B), the overtube 91 is pushed to advance by a predetermined distance so that the side opening 92A faces the jejunum-to-jejunum anastomosed portion F5, that is, the inlet of the afferent loop F9. Then the insertion tube 13A of the endoscope 13X is pulled back and bent so as to make the distal end portion 45 protrude from the side opening 92A. Since the protruded position is present just at the inlet of the afferent loop F9, the insertion tube 13A is simply pushed to pass along the afferent loop F9 without any other actions, as shown in FIG. 21(C), whereby the insertion tube 13A can be passed there easily. As being flexible, the overtube 91 can be pushed and made to advance along the afferent loop F9 with the use of the insertion tube 13A as a guide member. In this inserting operation, twisting the overtube 91 makes the insertion easier (FIGS. 21(D) and 21(E)).

Accordingly, similarly to the second embodiment, passing the endoscope 13X along the afferent loop F9 can be facilitated.

(Seventh Modification)

Figure 22:
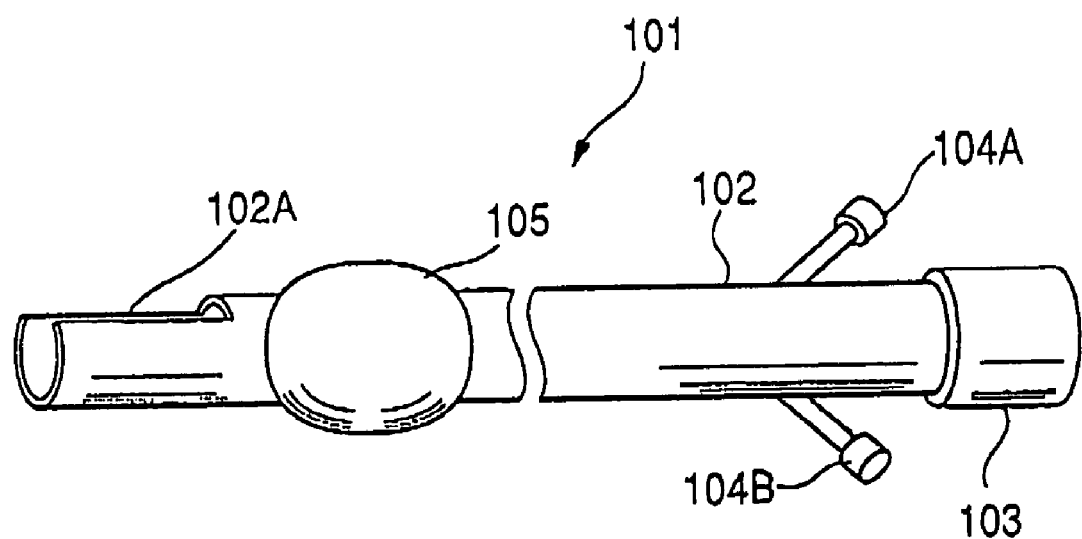
FIG. 22 is a partial perspective view showing an overtube according to a seventh modification.
Figure 23:
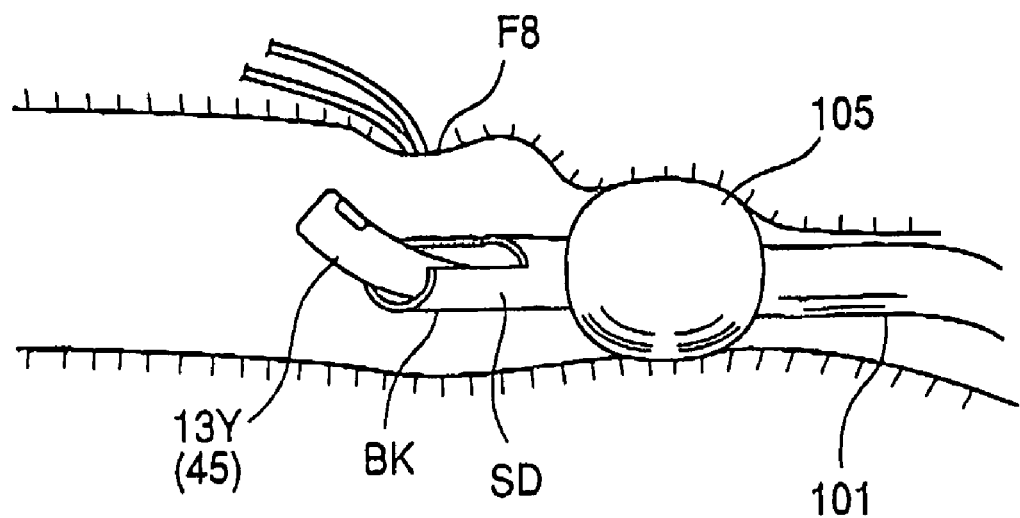
FIG. 23 explains part of the processes to approach the Vater's papilla according to the seventh modification.
Figure 24:
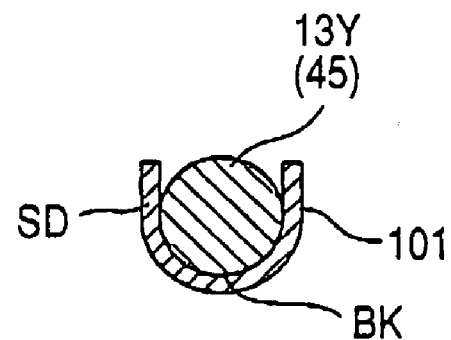
FIG. 24 explains the positional relationship between a second endoscope and an overtube, which is viewed axially in the seventh modification.

FIGS. 22-24 show a seventh modification, which still concerns another structure of the overtube.

An overtube 101 shown in FIG. 22 comprises a flexible tubular portion 102 made of resin material and having flexibility, a grip 103 formed integrally with an at-hand-side end of this flexible tubular portion 102, and an air-supply mouth ring 104A and a water-supply mouth ring 104B both formed from the flexible tubular portion 102. Furthermore, through a side wall residing in a distal end part of the flexible tubular portion 102, a slit 102A with a predetermined length is opened along its axial direction to communicate with the distal end opening. Incidentally it is not always necessary to load a balloon on this overtube 91. A balloon 105 similar to that has been described already is equipped at a distal-end-side predetermined position on the flexible tubular portion 102. The balloon 105 can be expanded and shrunk by selectively supplying to and discharging air from the air-supply mouth ring 104A.

Hence, when the second endoscope 13Y (side-viewing endoscope) is subjected to insertion for a treatment of pancreatic and biliary ducts, a back portion BK and side portions SD of the distal end portion of the overtube 101, which are other than the side opening 102A, positionally restrains the second endoscope 13Y, as shown in FIGS. 23 and 24. It is therefore easier to sustain the position of the distal end portion 45 relative to the Vater's papilla F8. In this restrained state as shown in FIG. 24, the second endoscope 13Y is elevated appropriately for the treatment of pancreatic and biliary ducts.

(Eighth Modification)

Figure 25:
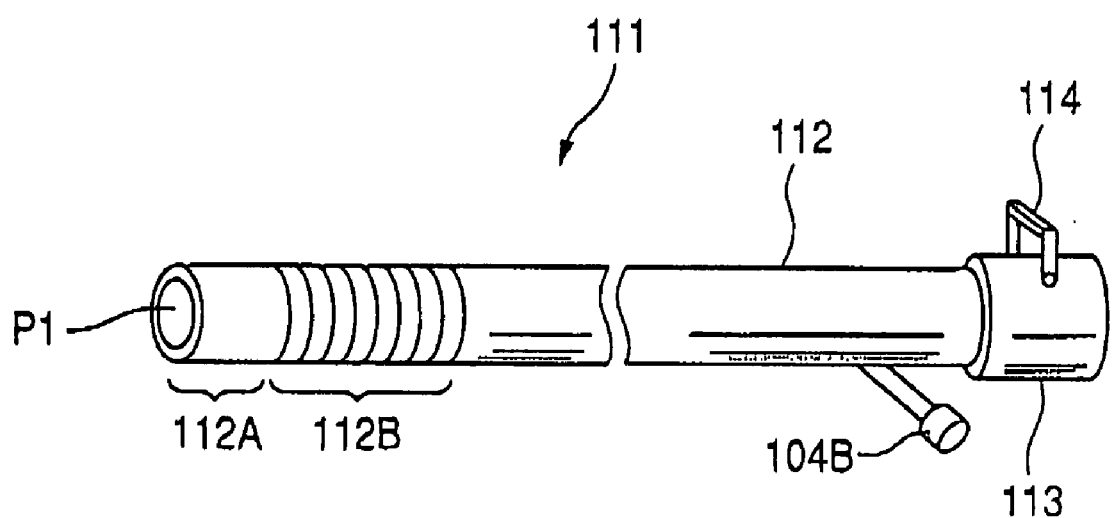
FIG. 25 is a partial perspective view showing an overtube according to an eighth modification.
Figure 26:
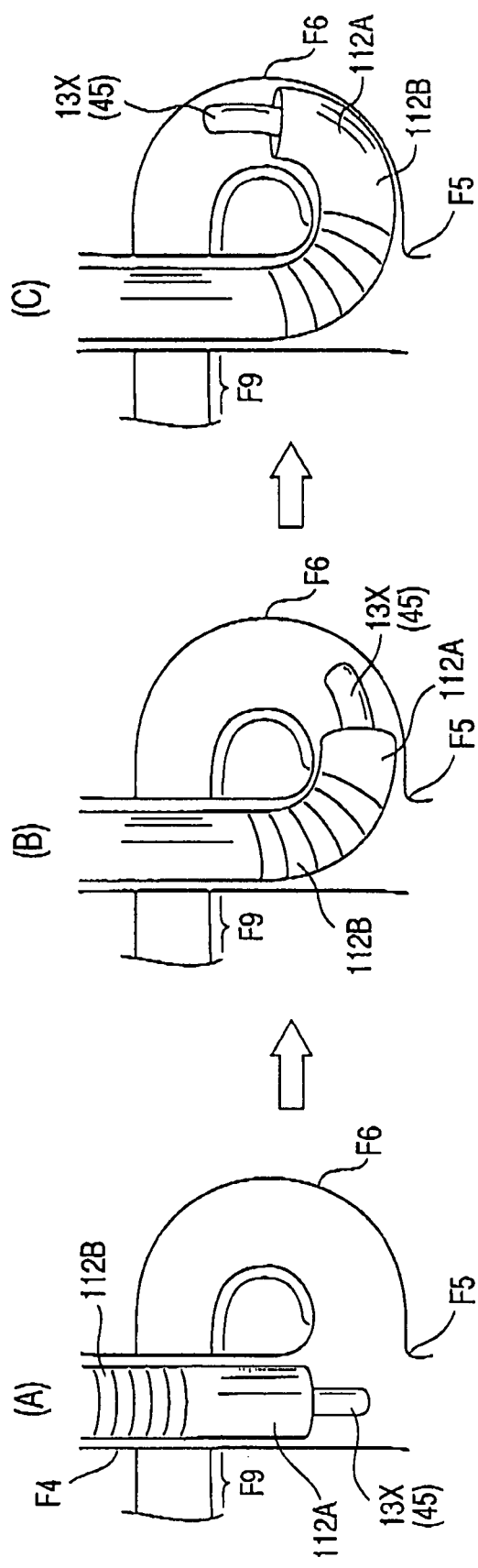
FIG. 26 explains part of the processes to approach the Vater's papilla according to the eighth modification.

FIGS. 25-26 show an eighth modification, which still concerns another structure of the overtube.

An overtube 111 shown in FIG. 25 comprises a flexible tubular portion 112 made of resin material and having flexibility and a grip 113 formed integrally with an at-hand-side portion of the flexible tubular portion 112. The flexible tubular portion 112 includes a distal end portion 112A, a bendable portion 112B formed adjacently to the distal end portion 112A and formed to have a predetermined axial length, and a water-supply mouth ring 104B positioned at a base-end-side predetermined position. The bendable portion 112B is structured to be bendable actively toward either up/down/right/left four directions (when viewed along the axial direction) or any two of the four directions by tow forces of wires (not shown). In FIG. 25, an operation lever 114 is attached to the grip 113, which operation lever 114 is for bending the bendable portion 112B in the two directions. Handling this operation lever 114 allows the wires (not shown; inserted to axially pass the flexible tubular portion 112) to give tow forces to the bendable portion 112B. Thus the bendable portion 112B can be bent in response to an operator's demand.

Thus, with the first endoscope 13X inserted through the insertion channel P1 of the overtube 111, the overtube 111 is orally inserted into the body. When the endoscope 13X reaches a predetermined position where forward-viewing endoscopic images capture the jejunum-to-jejunum anastomosed portion F5, the endoscope 13X is temporarily stopped from being inserted (refer to FIG. 26(A)). Then, as the overtube 111 is pushed to advance, the operator handles, in parallel with the advancement, the operation lever 114 to bend the bendable portion 112B at an almost right angle to be oriented toward the jejunum-to-jejunum anastomosed portion F5 (refer to FIG. 26(B)). As a result, the distal end portion 112A of the overtube 111 can be inserted deeply along the afferent loop F9, together with the distal and portion 45 of the insertion tube 13A of the first endoscope 13X (refer to FIG. 26(C)).

Incidentally, it is not always true that the overtube 111 is provided with the balloon. But when such a balloon is needed, it is preferred that the balloon is provided at a base-end-side part of the bendable portion. In the case that the balloon is equipped on the overtube 111, the positional fixing function given by the balloon may be used together in the insertion state shown in FIG. 26(A).

(Ninth Modification)

Figure 27:
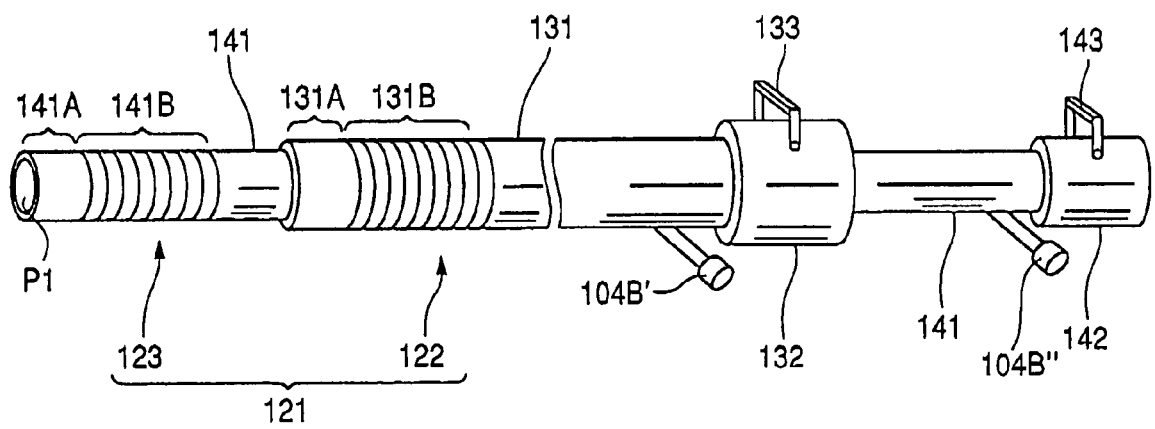
FIG. 27 is a partial perspective view showing an overtube according to a ninth modification.
Figure 28:
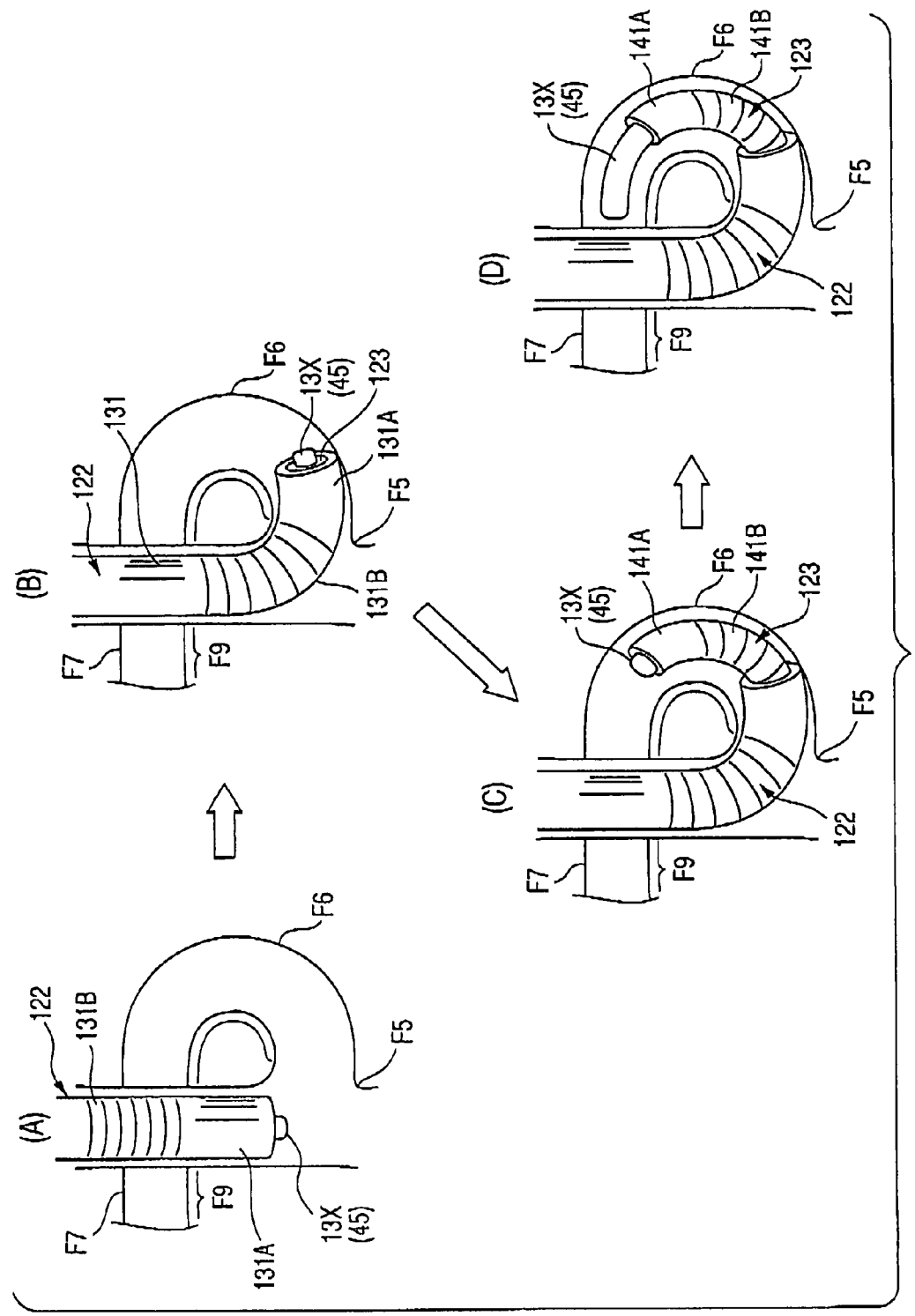
FIG. 28 explains part of the processes to approach the Vater's papilla according to the ninth modification.

FIGS. 27-28 show a ninth modification, which still concerns another structure of the overtube.

An overtube 121 shown in FIG. 27 is equipped with a cylindrical resin-made outer tube 122 having an insertion channel and a resin-made inner tube 123 to be inserted through the insertion channel of the outer tube 122.

Of these tubes, the outer tube 122 includes a resin-made flexible tubular portion 131 having flexibility and a grip 132 formed integrally with an at-hand-side end of the flexible tubular portion 131. The flexible tubular portion 131 includes a distal end portion 131A and a bendable portion 131B positioned next to the distal portion 131A and formed to have a predetermined axial length. This bendable portion 131B is structured to be bendable actively for example in the up/down/right/left four directions or any two of the four directions (when viewed along the axial direction) by tow forces of wires (not shown). In the structure shown in FIG. 27, the bendable portion 131B can be bent in two directions by handling an operation lever 133 attached to the grip 132. Handling the operation lever 133 allows wires to give tow forces to the bendable portion 131B, which wires are inserted to axially pass the flexible tubular portion 131. Thus the operator is able to bend the bendable portion 131B according to operator's demand.

The similar structure is true of the inner tube 123. That is, the inner tube 123 includes a resin-made flexible tubular portion 141 having flexibility and a grip 142 positioned next to the at-hand-side end of the flexible tubular portion 141. Further, the flexible tubular portion 141 includes a distal end portion 141A and a bendable portion 141B located next to the distal end portion 141A to have a axial predetermined length. The bendable portion 141B is structured to be bendable actively for example in the up/down/right/left four directions or any two of the four directions (when viewed along the axial direction) by tow forces of wires (not shown). An operation lever 143 to handle the bendable portion 141B is attached to the grip 142. Handling the operation lever 143 enables the wires, which axially pass the flexible tubular portion 141, to give tow forces to the bendable portion 141B, which can be bent according to operator's demand.

References 104B' and 104B" in FIG. 27 represent a water-supply mouth ring, respectively.

Hence, with the first endoscope 13X inserted through the insertion channel P1 of the overtube 121, the overtube 121 is orally inserted, during which forward-viewing images capture the jejunum-to-jejunum anastomosed portion F5 at a predetermined inserting position, whereat the insertion is temporarily stopped (refer to FIG. 28(A)). Then the operator handles the operation lever 133 of the outer tube 122 so that the bendable portion 131B is bent at an almost right angle to be directed toward the jejunum-to-jejunum anastomosed portion F5, concurrently with operations to make the outer tube 122 advance (refer to FIG. 28(B)).

Thus, together with the distal end portion 45 of the insertion tube 13A of the first endoscope 13X, the distal end portion 131A of the outer tube 122 (and the inner tube 123) can be inserted deeply along the afferent loop F9. When the outer tube 122 is inserted to some extent into the afferent loop F9, the operator makes the inner tube 123 protrude from the outer tube 122, while the inner tube 123 is bent (refer to FIG. 28(C)). Hence, the distal end of the inner tube 123 almost reaches a deep position in the afferent loop F9, which deep position is nearly the end of a curve of the afferent loop F9. After this, the operator extends the first endoscope 13X from the distal end of the inner tube 123 along the afferent loop F9.

In this way, the outer tube 122 is in charge of performing the bent operation needed to intrude into the afferent loop F9, the inner tube 123 is in charge of running to finish almost the jejunum-to-jejunum bent portion F6 which is a primary curve of the afferent loop F9, and then the endoscope 13X is in charge of running along a final moderate curved part of the duodenum F7. That is, the relatively thin, long, and sharp curve of the afferent loop F9 is covered by the three-step relaying bending operations. Hence the degree of bending necessary in each step is not so sharp, enabling the overtube 121 and the insertion tube 13A of the endoscope 13X to pass the afferent loop F9 smoothly and steadily.

In addition, the overtube 121 may not always be equipped with a balloon. When the balloon is equipped on the overtube 121, it is preferred that the balloon is present at a base-end-side part of the bendable portion.

Of course, a balloon may be equipped on the outer tube 122 of the overtube 121 to utilize the positional fixing function on the balloon in the state shown in FIG. 28(A).

Tenth Embodiment

Figure 29:
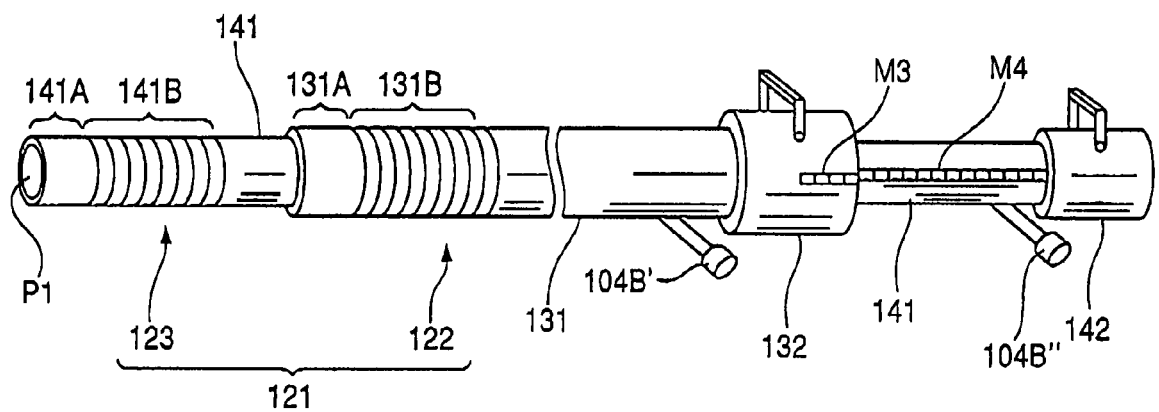
FIG. 29 is a side view showing an overtube according to a tenth modification.

FIG. 29 shows a tenth modification, which concerns a modified form (positioning) of the overtube 121 shown in FIG. 27, which is according to the ninth modification.

Specifically, as shown in FIG. 29, to achieve the positioning between the outer and inner tubes 122 and 123 in the circumferential direction around the axial direction, markers are adopted. A marker M3 is put on the grip 132 of the outer tube 122, while a marker M4 is put on the grip 142 of the inner tube 123. Matching these markers M3 and M4 with each other leads to positioning both tubes 122 and 123 in the circumferential direction, whereby the bending directions thereof can be matched with each other. In addition, the length of the inner tube 123 protruded from the outer tube 122 can be measured.

(Eleventh Modification)

Figure 30:
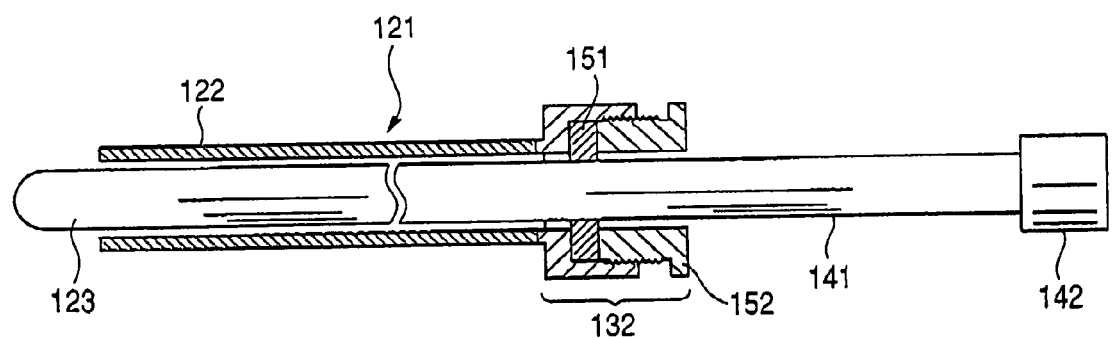
FIG. 30 is a partial sectional view taken axially to show the structure of an overtube according to an eleventh modification.
Figure 31:
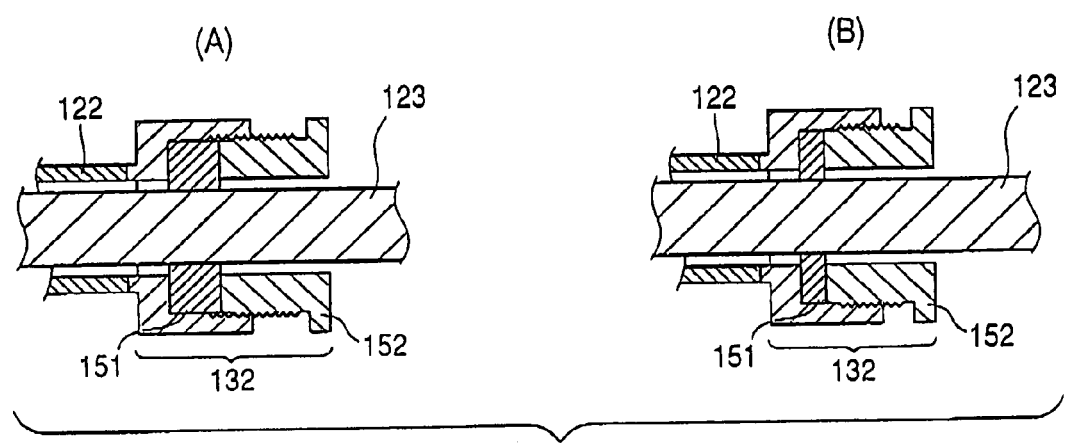
FIG. 31 is a partial sectional view explaining the operations of a lock mechanism to an overtube in the eleventh modification.

FIGS. 30-31 show an eleventh modification, which concerns a modified form (lock mechanism) of the overtube 121 shown in FIG. 27, which is according to the ninth modification.

Practically the overtube 121 includes the outer and inner tubes 122 and 123, as described already. Inside the grip 132 of the outer tube 122, an elastic ring 151 is incorporated which exhibits a higher friction coefficient relative to the outer surface of the flexible tubular portion 141 of the inner tube 123. This elastic ring 151 can be pushed detachably by a knob 152 that engages with a thread formed on the inner surface of the grip 132.

Hence, as shown in FIG. 31(A), when the knob 152 is loosened, the elastic ring 151 is not pushed, so that the inner diameter of the elastic ring 151 is larger. In this state, the inner tube 123 passes and moves through the insertion port of the outer tube 122 without any interference. Tightening the knob 152 causes a reduction in the inner diameter of the elastic ring 151 as shown in FIG. 31(B), thus enabling the inner wall portion to push the inner tube 123.

Therefore, the inner and outer tubes 123 and 122 can be locked with each other at a desired position in the axial and circumferential directions.

Incidentally, this lock mechanism is not limited to the application employed between the outer and inner tubes of the overtube. For instance, as a locking means, this lock mechanism can also be applied between the overtube and an endoscope to be inserted. In such a case, the foregoing elastic ring and knob are loaded on the overtube, in which the lock function is given to the insertion tube of the endoscope.

(Twelfth Modification)

Figure 32:
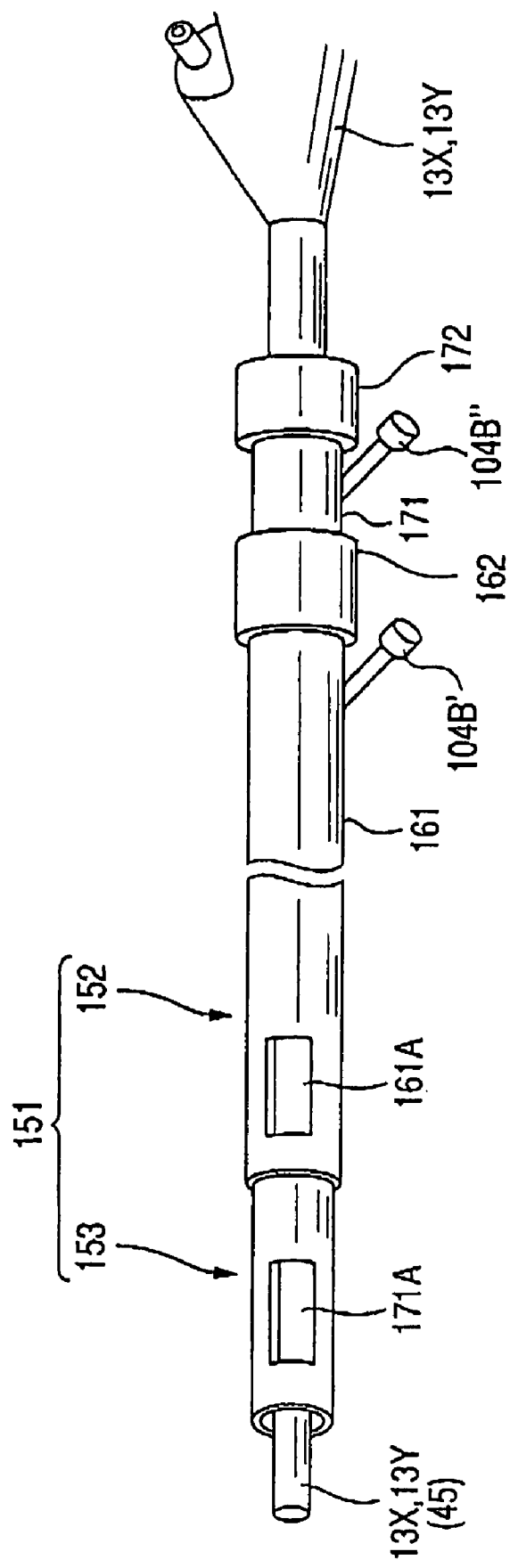
FIG. 32 is a partial perspective view showing an overtube according to a twelfth modification.
Figure 33:
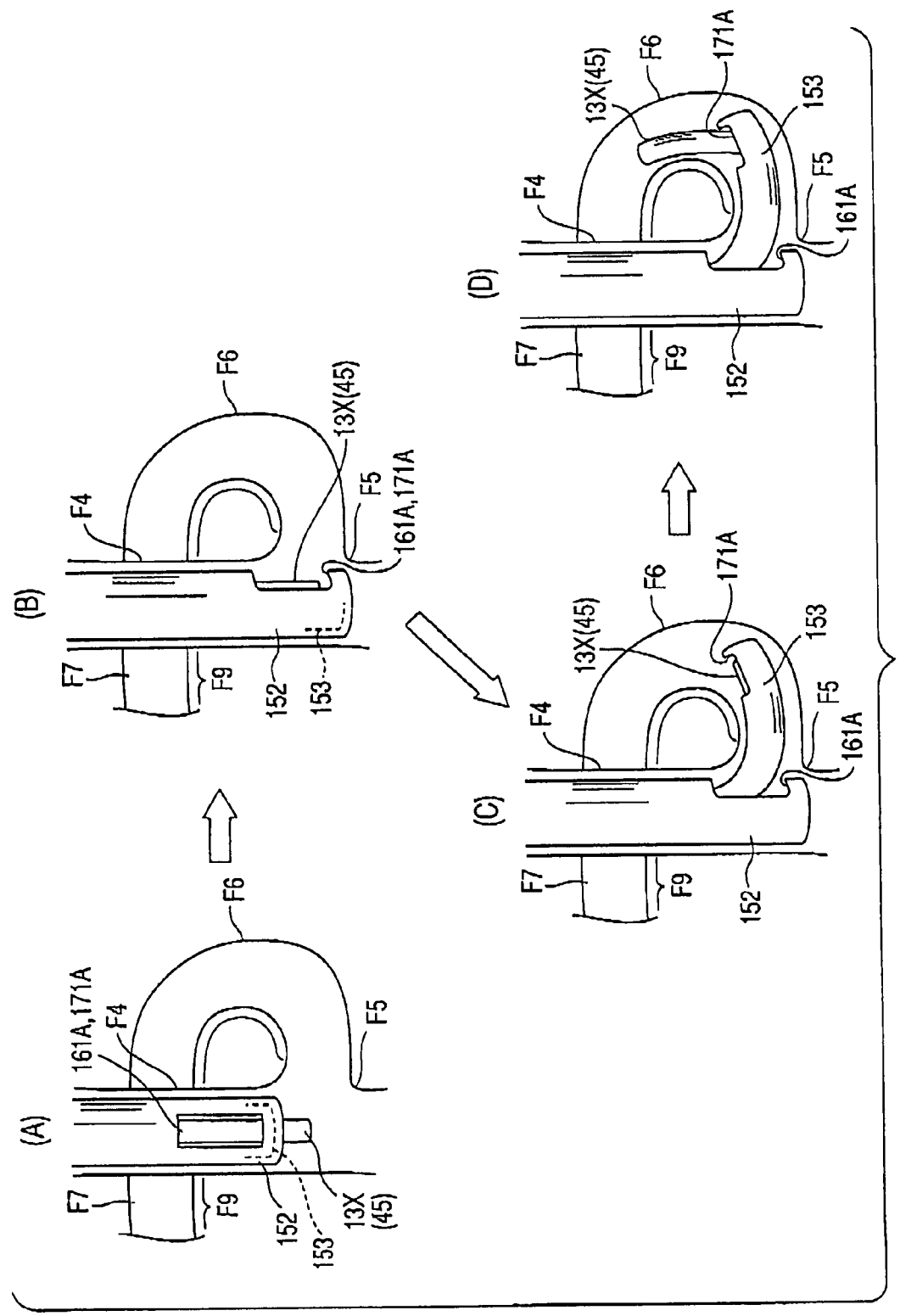
FIG. 33 explains part of the processes to approach the Vater's papilla according to the twelfth modification.

FIGS. 32-33 show a twelfth modification, which still concerns a further modified form of the overtube. In particular, this modification concerns an overtube, which is equipped with outer and inner tubes, providing the endoscope with a guide during passing the sharpest curve of the afferent loop F9, i.e., a part ranging from the jejunum-to-jejunum anastomosed portion F5 to the jejunum-anastomosed bent portion.

As shown in FIG. 32, an overtube 151 is equipped with an outer tube 152 and an inner tube 153. The outer tube 152 includes a flexible tubular portion 161 having an insertion channel and a grip 162 formed integrally with an axial base-side end of the flexible tubular portion 161. At a distal-side predetermined position of the flexible tubular portion 161, a side opening 161A is formed in the axial direction thereof. The inner tube 153 is made of a resin and has a high flexibility, and is subjected to insertion into the insertion channel of the outer tube 152. Like the foregoing, the inner tube 153 includes a flexible tubular portion 171 having an insertion channel and a grip 172 formed integrally with an axial base-side end of the flexible tubular portion 171. At a distal-side predetermined position of the flexible tubular portion 171, a side opening 171A is formed in the axial direction thereof.

The insertion tube 13A of the first endoscope 13X or the second endoscope 13Y, which is selected, is inserted into the insertion channel of the inner tube 153.

Practically, in a state where the first endoscope 13X is inserted through the insertion channel of the inner tube 153 and the inner tube 153 is inserted through the insertion channel of the outer tube 152, an operator observes forward-viewing endoscopic images, during which time the operation inserts orally the overtube 151 and the first endoscope 13X to reach the jejunum-to-jejunum anastomosed portion F5. That is, as shown in FIG. 33(A), the outer tube 152 reaches a predetermined position just before the jejunum-to-jejunum anastomosed portion F5. Then, as shown in FIG. 33(B), the operator pulls back the first endoscope 13X so that the distal end of the first endoscope 13X is hidden within the inner tube 153, and the operator manually rotates the outer tube 152 to orient its side opening 161A toward the jejunum-to-jejunum anastomosed portion F5, i.e., the inlet of the afferent loop F9. This operation allows the side opening 161A and the inlet of the afferent loop F9 to be positioned with each other.

After this, as shown in FIG. 33(C), the operator pushes the inner tube 153 by a predetermined length from the side opening 161A of the outer tube 152 toward the afferent loop F9. By this operation, the inner tube 153 is allowed to reach almost half the jejunum-anastomosed bent portion F6. This inner tube 153 has a sufficient flexibility, the inner tube 153 can be reached deeply, as shown in the figure, as almost half as the jejunum-anastomosed bent portion F6 reasonably, without positive bending actions like the present example. Of course, the inner tube 153 may be bent positively for insertion or a slit may be formed to make it easier that the inner tube is bent further passively.

When the insertion of the inner tube 153 is completed, the operator extends the first endoscope 13X, from the side opening 171A of the inner tube 153, along the remaining part of the afferent loop F9 (refer to FIG. 33(D)). Since being already guided until almost half of the afferent loop F9 by the outer and inner tubes 152 and 153, it is easier for the first endoscope 13X to advance continuously from the former insertion. Thus this endoscope 13X can be extended to reach the Vater's papilla F8, with imaging and treatments performed necessary thereat.

When the second endoscope 13Y is fed instead of the first endoscope 13X, the guide path already provided by the outer and inner tubes 152 and 153 can be used to allow the second endoscope 13Y to pass through the afferent loop F9 so as to reach the Vater's papilla F8 smoothly in a short period of time.

As a result, like the foregoing embodiments and modifications, it is possible that the endoscope 13 is able to pass, smoothly and easily, the relatively thin and longer afferent loop F9 with the inlet almost perpendicular to the jejunum F4. The insertion can be facilitated.

Incidentally when a balloon is put on the distal end portion of the inner tube 153, the balloon may be expanded, in the state of FIG. 33(D), to be fixed positionally to the inner wall of the afferent loop F9. This positional fixing provides a fulcrum to assist the extension of the first endoscope 13X.

(Thirteenth Modification)

Figure 34:
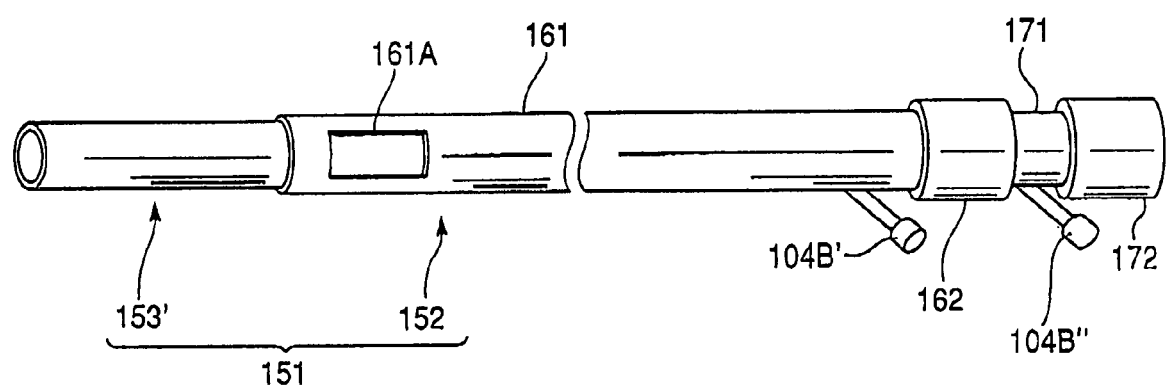
FIG. 34 is a partial perspective view showing an overtube according to a thirteenth modification.
Figure 35:
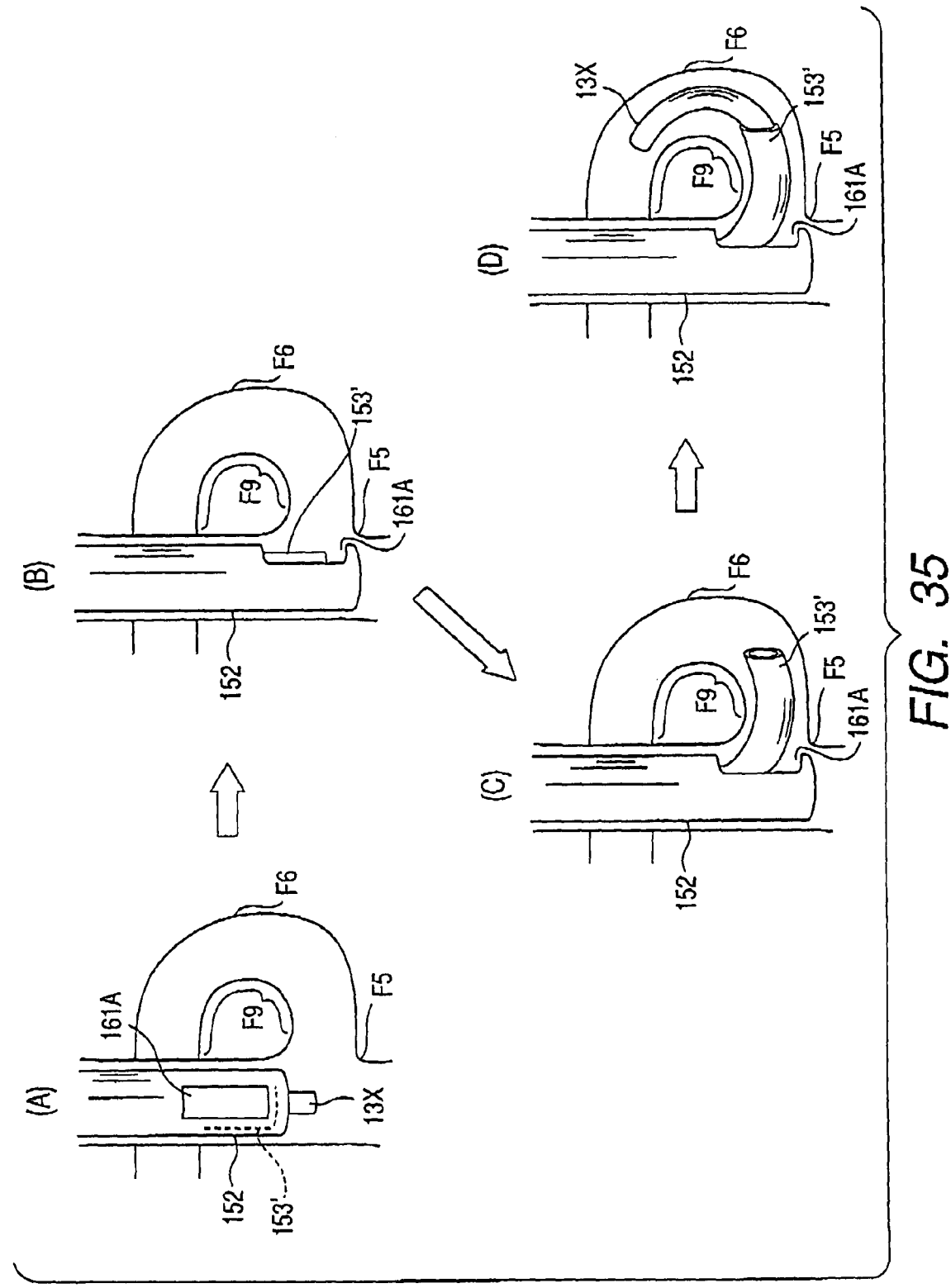
FIG. 35 explains part of the processes to approach the Vater's papilla according to the thirteenth modification.

FIGS. 34-35 show a thirteenth modification, which still concerns a further modified form of the twelfth modification. Part of the reference numerals used in this modification is diverted from those of the twelfth modification.

In the thirteenth modification, the overtube 151 has the outer tube 152 and an inner tube 153'. In particular, as shown in FIG. 34, the inner tube 153' has no side opening.

According to this configuration, as shown in FIG. 35(A)-(D), the similar operations and advantages to those in the foregoing twelfth modification can be obtained. Particularly, as understood from FIG. 35(C), (D), while the insertion tube 13A of the first endoscope 13X is made to advance from the frontal opening of the inner tube 153' while the insertion tube is bent. This allows the overtube 151 to smoothly advance along the jejunum-to-jejunum anastomosed portion F5 and the jejunum-anastomosed bent portion F6.

Further, the inner tube 153' can be made to advance further by running it on and along the insertion tube 13A, so that, like the first embodiment, it is possible to provide endoscope guide means till a vicinity of the Vater's papilla F8 by using the combination of the outer tube 152 and the inner tube 153'.

(Fourteenth Modification)

Figure 36:
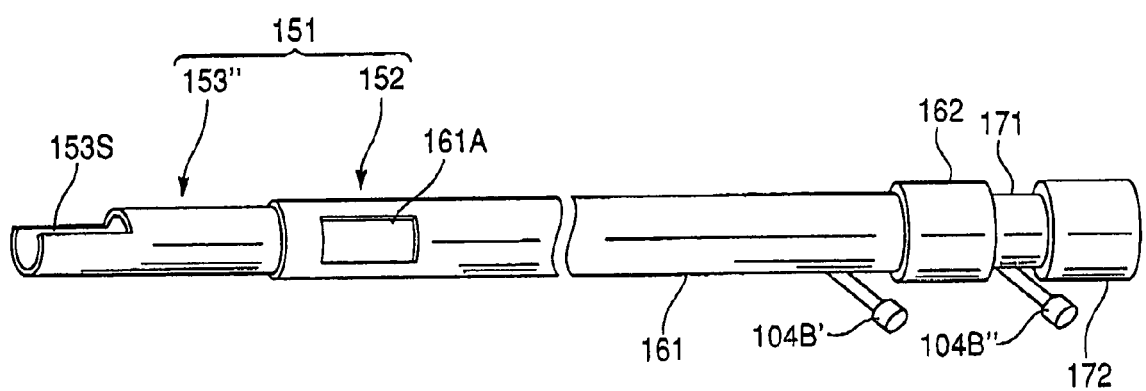
FIG. 36 is a partial perspective view showing an overtube according to a fourteenth modification.
Figure 37:
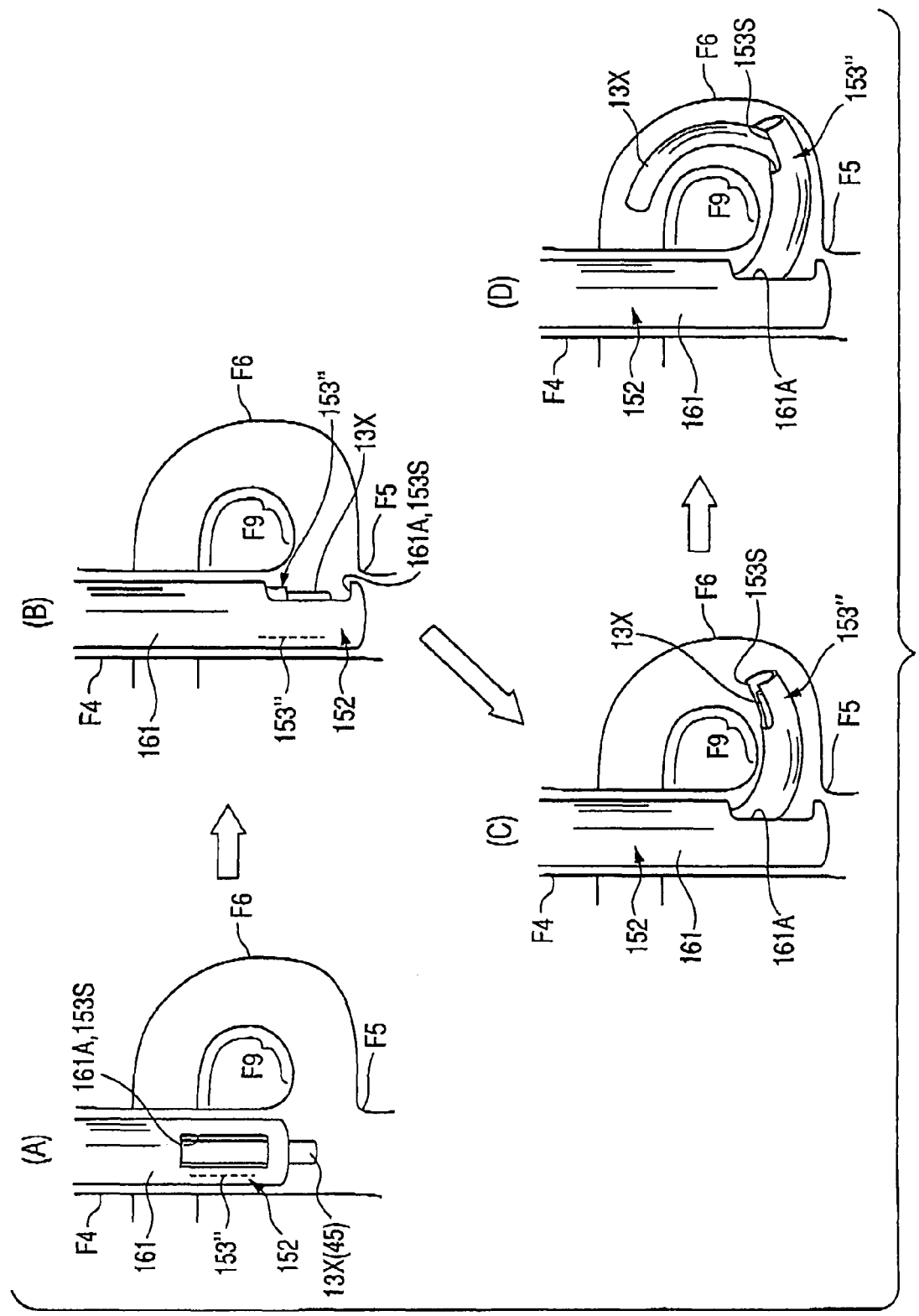
FIG. 37 explains part of the processes to approach the Vater's papilla according to the fourteenth modification.

FIGS. 36-37 show a fourteenth modification, which still concerns a further modified form of the twelfth modification. Part of the reference numerals used in this modification is diverted from those of the twelfth modification.

In the fourteenth modification, the overtube 151 comprises the outer tube 152 and an inner tube 153'. Specifically, as shown in FIG. 36, the inner tube 153", has a slit 153S formed at the distal end portion thereof and formed to extend to have a predetermined length continued from the frontal opening.

According to this configuration, as shown in FIG. 37(A)-(D), the similar operations and advantages to those in the foregoing twelfth modification can be obtained. Particularly, as understood from FIG. 37(C), (D), while the insertion tube 13A of the first endoscope 13X is made to advance from the slit 153S of the inner tube 153' while the insertion tube is bent.

This provides the similar operations and advantages to those in the third modification.

Incidentally, the scope of the present invention will not be limited to the configurations described in the foregoing embodiments and their various modifications, but the present invention may be reduced into practice in appropriate modes combined with conventional known structures, without departing from the scope of the present invention described in the appended claims.

What is claimed is:

1. A method of either diagnosing or treating a Vater's papilla and tissue located adjacently thereto, comprising:
    a first step in which a first endoscope is inserted into an insertion channel of an overtube provided with only a single balloon, the single balloon being provided on the overtube close to a distal end of the overtube and being selectively expandable or shrinkable;
    a second step in which, with the first endoscope inserted through the insertion channel of the overtube and the balloon shrunk on the overtube, the first endoscope and the overtube are orally inserted into an object being examined toward a jejunum of the object;
    a third step in which, when a distal end portion of the insertion tube of the first endoscope reaches a position facing a jejunum-to-jejunum anastomosed portion of the jejunum, the distal end of the overtube is positionally fixed to the jejunum by making the balloon expand to touch the jejunum;
    a fourth step in which the distal end portion of the insertion tube of the first endoscope is directed toward the jejunum-to-jejunum anastomosed portion;
    a fifth step in which the directed insertion tube is made to advance via the jejunum-to-jejunum anastomosed portion and a jejunum-anastomosed bent portion to enable the distal end portion of the insertion tube to be positioned adjacently to a Vater's papilla of a duodenum of the object;
    a sixth step in which the distal end of the overtube is released from being positionally fixed to the jejunum by making the balloon shrink;
    a seventh step in which the overtube is made to advance along the insertion tube of the first endoscope such that the distal end of the overtube is positioned adjacently to the Vater's papilla;
    an eighth step in which the distal end of the overtube is fixed to the duodenum by making the balloon expand to touch the duodenum;
    a ninth step in which the first endoscope is pulled out of the insertion channel of the overtube; and
    a tenth step in which a second endoscope is inserted into the insertion channel of the overtube to enable a distal end portion of an insertion tube of the second endoscope to be protruded from the distal end of the overtube and position the distal end portion adjacently to the Vater's papilla, the second endoscope being for diagnosis or treatment of the Vater's papilla and the tissue located adjacently thereto.

2. The treatment method of claim 1, wherein the first endoscope is either a forward-viewing endoscope or an oblique-viewing endoscope and the second endoscope is a side-viewing endoscope.

3. The treatment method of claim 1, wherein the fourth step uses the overtube to change a direction of the distal end portion of the first endoscope to the jejunum-to-jejunum anastomosed portion.

4. The treatment method of claim 3, wherein
    the fourth step is a step in which, when the distal end portion of the overtube has reached the jejunum-to-jejunum anastomosed portion, the overtube is rotated on the axial direction so as to direct a cut portion of the distal end portion of the overtube toward the jejunum-to-jejunum anastomosed portion, the cut portion being formed by cutting part of the overtube, the cut part including at least a wall portion of the overtube which exists in the axial direction thereof, and
    the fifth step is a step in which the distal end portion of the insertion tube of the first endoscope is made to advance toward the jejunum-to-jejunum anastomosed portion via the cut portion of the overtube.

5. The treatment method of claim 4, wherein the cut portion is an oblique opening which is cut obliquely to the axial direction of the overtube.

6. The treatment method of claim 4, wherein the cut portion is formed into a slit opened over a preset length of the overtube in the axial direction thereof.

7. The treatment method of claim 3, wherein
the fourth step is a step in which, when the distal end portion of the overtube has reached the jejunum-to-jejunum anastomosed portion, the overtube is bent so as to be directed toward the jejunum-to-jejunum anastomosed portion, and
the fifth step is a step in which the distal end portion of the insertion tube of the first endoscope is made to advance toward the jejunum-to-jejunum anastomosed portion via the distal end portion of the overtube.

8. The treatment method of claim 3, wherein
the fourth step is a step in which, when the distal end portion of the overtube has reached the jejunum-to-jejunum anastomosed portion, the overtube is rotated on the axial direction so as to direct a side opening of the distal end portion of the overtube toward the jejunum-to-jejunum anastomosed portion, the side opening being formed through a wall portion of the distal end portion of the overtube, and
the fifth step is a step in which the distal end portion of the insertion tube of the first endoscope is made to advance toward the jejunum-to-jejunum anastomosed portion via the side opening of the overtube.

* * * * *